United States Patent
Zverlov et al.

(10) Patent No.: US 10,907,140 B2
(45) Date of Patent: Feb. 2, 2021

(54) MUTANT BETA-GLUCOSIDASE VARIANTS WITH INCREASED THERMOSTABILITY

(71) Applicant: Technische Universitaet Muenchen, Munich (DE)

(72) Inventors: Vladimir Zverlov, Munich (DE); Wolfgang Schwarz, Munich (DE); Roman Prechtl, Freising (DE); Benedikt Leis, Moosburg a.d. Isar (DE); Claudia Held, Freising (DE); Wolfgang Liebl, Freising (DE)

(73) Assignee: Technische Universitaet Muenchen, Munich (DE)

( * ) Notice: Subject to any disclaimer, the term of this patent is extended or adjusted under 35 U.S.C. 154(b) by 93 days.

(21) Appl. No.: 15/767,066

(22) PCT Filed: Sep. 5, 2016

(86) PCT No.: PCT/EP2016/070804
§ 371 (c)(1),
(2) Date: Apr. 9, 2018

(87) PCT Pub. No.: WO2017/063787
PCT Pub. Date: Apr. 20, 2017

(65) Prior Publication Data
US 2019/0071658 A1 Mar. 7, 2019

(30) Foreign Application Priority Data

Oct. 15, 2015 (DE) .......................... 10 2015 117 534

(51) Int. Cl.
*C12N 9/42* (2006.01)
*C12N 15/86* (2006.01)
*C12P 19/14* (2006.01)

(52) U.S. Cl.
CPC .......... *C12N 9/2445* (2013.01); *C12N 15/86* (2013.01); *C12P 19/14* (2013.01); *C12Y 302/01021* (2013.01)

(58) Field of Classification Search
CPC . C12Y 302/01021; C12P 19/14; C12N 15/86; C12N 9/2445
See application file for complete search history.

(56) References Cited

U.S. PATENT DOCUMENTS

| | | | | |
|---|---|---|---|---|
| 8,101,393 B2 * | 1/2012 | Gray | .................... | C12N 9/2437 435/209 |
| 8,354,266 B2 * | 1/2013 | Li | ........................ | C07K 14/33 435/252.31 |
| 8,715,996 B2 * | 5/2014 | Baidyaroy | .......... | C12N 9/2445 435/207 |
| 10,294,484 B2 * | 5/2019 | Brevnova | .............. | C12N 15/52 |

FOREIGN PATENT DOCUMENTS

| | | |
|---|---|---|
| EP | 2410061 A1 | 1/2012 |
| WO | 2010/099500 A2 | 9/2010 |
| WO | 2010/148148 A2 | 12/2010 |

OTHER PUBLICATIONS

Banerjee et al., Improving enzymes for bionass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Olson & Cepuritis, Ltd.

(57) ABSTRACT

A mutant β-glucosidase polypeptide exhibits enhanced thermostability and has the amino acid sequence:

MAKFPRDFVWGTATSSYQIEGAVNEDGRTPSIWDTFSKTX$_1$GKTYKGHT

GDVACDHYHRYKEDVEILKEIGVKAYRFSIAWPRIFPEEGKYNPKGMDF

YKKLIDELQKRDIX$_2$PAATIYHWDLPQWAYDKGGGWLNRESIKWYVEYA

TKLFEELGDAIPLWITHNEPWCSSILSYGIGEHAPGHKNYREALIAAHH

ILLSHGEAVKAFREMNIKGSKIGITLNLTPAYPASEKEEDKLAAQYADG

FANRWELDPIFKGNYPEDMMELYSKIIGEFDFIKEGDLETISVPIDFLG

X$_3$NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYX$_4$TQKRILKDSALWYK

EVIX$_5$DDGIED, wherein
X$_1$ is selected from E, P, T, M, A, S and G;
X$_2$ is selected from V, K, R and H;
X$_3$ is selected from I, L, M, P, T and A;
X$_4$ is selected from T, E, D, N, Q, M and P; and
X$_5$ is selected from L, R, K and H.

22 Claims, 5 Drawing Sheets
Specification includes a Sequence Listing.

(56) References Cited

OTHER PUBLICATIONS

Arrizubieta M J et al: "Increased thermal resistance and modification of the catalytic properties of a beta-glucosidase by random mutagenesis and in vitro recombination", The Journal of Biological Chemistry, vol. 275, No. 37, Sep. 15, 2000, pp. 28843-28848.
Lucas, S. et al.; Beta glucosidase from Thermobacterium xylanolyticum, Jul. 27, 2011, URL:http://www.uniprot.org/uniprot/F6BL86. txt.
Anonymous: Duniprot:X1E501,May 14, 2014, XP055314301, Retrieved from the Internet: URL:http://ibis.internal.epo.o org/exam/dbfe.
Anonymous: "Thermoanaerobacter indiensis BSB-33 genomic scaffold B044DRAFT scaffol—Nucleotide—NCBI", Aug. 14, 2015, XP055314497, Retrieved from the Internet: URL:https://www.ncbi.nlm.nih.gov/nuccore/N.

\* cited by examiner

SEQUENCE LISTING

```
<160> NUMBER OF SEQ ID NOS: 52

<210> SEQ ID NO 1
<211> LENGTH: 447
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (40)..(40)
<223> OTHER INFORMATION: Xaa is selected from Glu, Pro, Thr, Met, Ala,
      Ser and Gly
<220> FEATURE:
<221> NAME/KEY: VARIANT
<222> LOCATION: (111)..(111)
<223> OTHER INFORMATION: Xaa is selected from Val, Lys, Arg and His
<220> FEATURE:
<221> NAME/KEY: VARIANT
<222> LOCATION: (293)..(293)
<223> OTHER INFORMATION: Xaa is selected from Val, Ile, Leu, Met, Pro,
      Thr and Ala
<220> FEATURE:
<221> NAME/KEY: VARIANT
<222> LOCATION: (423)..(423)
<223> OTHER INFORMATION: Xaa is selected from Thr, Glu, Asp, Asn, Gln,
      Met and Pro
<220> FEATURE:
<221> NAME/KEY: VARIANT
<222> LOCATION: (441)..(441)
<223> OTHER INFORMATION: Xaa is selected from Leu, Arg, Lys and His

<400> SEQUENCE: 1

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Xaa Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Xaa Pro
            100                 105                 110

Ala Ala Thr Ile Tyr His Trp Asp Leu Pro Gln Trp Ala Tyr Asp Lys
        115                 120                 125
```

```
Gly Gly Gly Trp Leu Asn Arg Glu Ser Ile Lys Trp Tyr Val Glu Tyr
130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
                180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
            275                 280                 285

Asp Phe Leu Gly Xaa Asn Tyr Tyr Thr Arg Ser Ile Val Lys Tyr Asp
                290                 295                 300

Glu Asp Ser Met Leu Lys Ala Glu Asn Val Pro Gly Pro Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
                355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Xaa Thr Gln Lys Arg Ile Leu Lys Asp Ser
                420                 425                 430

Ala Leu Trp Tyr Lys Glu Val Ile Xaa Asp Asp Gly Ile Glu Asp
                435                 440                 445
```

<210> SEQ ID NO 2
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: Variant
<222> LOCATION: (111)..(111)
<223> OTHER INFORMATION: Xaa is selected from Val, Lys, Arg and His
<220> FEATURE:
<221> NAME/KEY: Variant
<222> LOCATION: (293)..(293)
<223> OTHER INFORMATION: Xaa is selected from Val, Ile, Leu, Met, Pro,
      Thr and Ala
<220> FEATURE:
<221> NAME/KEY: Variant
<222> LOCATION: (423)..(423)

```
<223> OTHER INFORMATION: Xaa is selected from Thr, Glu, Asp, Asn, Gln,
      Met and Pro
<220> FEATURE:
<221> NAME/KEY: Variant
<222> LOCATION: (441)..(441)
<223> OTHER INFORMATION: Xaa is selected from Leu, Arg, Lys and His

<400> SEQUENCE: 2

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65              70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Xaa Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145             150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225             230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Xaa Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305             310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
```

-continued

```
                370                 375                 380
Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Xaa Thr Gln Lys Arg Ile Leu Lys Asp Ser
                420                 425                 430

Ala Leu Trp Tyr Lys Glu Val Ile Xaa Asp Asp Gly Ile Glu Asp
            435                 440                 445

<210> SEQ ID NO 3
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: Variant
<222> LOCATION: (40)..(40)
<223> OTHER INFORMATION: Xaa is selected from Glu, Pro, Thr, Met, Ala,
      Ser and Gly
<220> FEATURE:
<221> NAME/KEY: Variant
<222> LOCATION: (293)..(293)
<223> OTHER INFORMATION: Xaa is selected from Val, Ile, Leu, Met, Pro,
      Thr and Ala
<220> FEATURE:
<221> NAME/KEY: Variant
<222> LOCATION: (423)..(423)
<223> OTHER INFORMATION: Xaa is selected from Thr, Glu, Asp, Asn, Gln,
      Met and Pro
<220> FEATURE:
<221> NAME/KEY: Variant
<222> LOCATION: (441)..(441)
<223> OTHER INFORMATION: Xaa is selected from Leu, Arg, Lys and His

<400> SEQUENCE: 3

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Xaa Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190
```

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
            275                 280                 285

Asp Phe Leu Gly Xaa Asn Tyr Tyr Thr Arg Ser Ile Val Lys Tyr Asp
            290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
            370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Xaa Thr Gln Lys Arg Ile Leu Lys Asp Ser
            420                 425                 430

Ala Leu Trp Tyr Lys Glu Val Ile Xaa Asp Asp Gly Ile Glu Asp
            435                 440                 445

<210> SEQ ID NO 4
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: Variant
<222> LOCATION: (40)..(40)
<223> OTHER INFORMATION: Xaa is selected from Glu, Pro, Thr, Met, Ala,
    Ser and Gly
<220> FEATURE:
<221> NAME/KEY: Variant
<222> LOCATION: (111)..(111)
<223> OTHER INFORMATION: Xaa is selected from Val, Lys, Arg and His
<220> FEATURE:
<221> NAME/KEY: Variant
<222> LOCATION: (423)..(423)
<223> OTHER INFORMATION: Xaa is selected from Thr, Glu, Asp, Asn, Gln,
    Met and Pro
<220> FEATURE:
<221> NAME/KEY: Variant
<222> LOCATION: (441)..(441)
<223> OTHER INFORMATION: Xaa is selected from Leu, Arg, Lys and His

<400> SEQUENCE: 4

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Xaa Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Xaa Pro
            100                 105                 110

Ala Ala Thr Ile Tyr His Trp Asp Leu Pro Gln Trp Ala Tyr Asp Lys
            115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
            165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
            245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
            325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
            405                 410                 415

Ile Val Tyr Val Asp Tyr Xaa Thr Gln Lys Arg Ile Leu Lys Asp Ser
            420                 425                 430

Ala Leu Trp Tyr Lys Glu Val Ile Xaa Asp Asp Gly Ile Glu Asp

```
<210> SEQ ID NO 5
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: Variant
<222> LOCATION: (40)..(40)
<223> OTHER INFORMATION: Xaa is selected from Glu, Pro, Thr, Met, Ala,
      Ser and Gly
<220> FEATURE:
<221> NAME/KEY: Variant
<222> LOCATION: (111)..(111)
<223> OTHER INFORMATION: Xaa is selected from Val, Lys, Arg and His
<220> FEATURE:
<221> NAME/KEY: Variant
<222> LOCATION: (293)..(293)
<223> OTHER INFORMATION: Xaa is selected from Val, Ile, Leu, Met, Pro,
      Thr and Ala
<220> FEATURE:
<221> NAME/KEY: Variant
<222> LOCATION: (441)..(441)
<223> OTHER INFORMATION: Xaa is selected from Leu, Arg, Lys and His

<400> SEQUENCE: 5

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
                20                  25                  30

Trp Asp Thr Phe Ser Lys Thr Xaa Gly Lys Thr Tyr Lys Gly His Thr
            35                  40                  45

Gly Asp Val Ala Cys Asp His Tyr His Arg Tyr Lys Glu Asp Val Glu
        50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Xaa Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
```

```
                    260                 265                 270
Phe Asp Phe Ile Lys Glu Gly Asp Leu Glu Thr Ile Ser Val Pro Ile
                275                 280                 285

Asp Phe Leu Gly Xaa Asn Tyr Tyr Thr Arg Ser Ile Val Lys Tyr Asp
            290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
        370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Xaa Asp Asp Gly Ile Glu Asp
        435                 440                 445

<210> SEQ ID NO 6
<211> LENGTH: 447
<212> TYPE: PRT
<213> ORGANISM: Artificial Sequence
<220> FEATURE:
<223> OTHER INFORMATION: Synthetic Polypeptide
<220> FEATURE:
<221> NAME/KEY: Variant
<222> LOCATION: (40)..(40)
<223> OTHER INFORMATION: Xaa is selected from Glu, Pro, Thr, Met, Ala,
      Ser and Gly
<220> FEATURE:
<221> NAME/KEY: Variant
<222> LOCATION: (111)..(111)
<223> OTHER INFORMATION: X is selected from V, K, R and H
<220> FEATURE:
<221> NAME/KEY: Variant
<222> LOCATION: (293)..(293)
<223> OTHER INFORMATION: Xaa is selected from Val, Ile, Leu, Met, Pro,
      Thr and Ala
<220> FEATURE:
<221> NAME/KEY: Variant
<222> LOCATION: (423)..(423)
<223> OTHER INFORMATION: Xaa is selected from Thr, Glu, Asp, Asn, Gln,
      Met and Pro

<400> SEQUENCE: 6

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Xaa Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80
```

```
Pro Arg Ile Phe Pro Glu Glu Gly Lys Tyr Asn Pro Lys Gly Met Asp
                 85                  90                  95

Phe Tyr Lys Lys Leu Ile Asp Glu Leu Gln Lys Arg Asp Ile Xaa Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Xaa Asn Tyr Tyr Thr Arg Ser Ile Val Lys Tyr Asp
    290                 295                 300

Glu Asp Ser Met Leu Lys Ala Glu Asn Val Pro Gly Pro Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Xaa Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 7
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 7
```

-continued

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
```

```
                420             425             430
Ala Leu Trp Tyr Lys Glu Val Ile Leu Asp Asp Gly Ile Glu Asp
            435             440             445

<210> SEQ ID NO 8
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 8

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
                100                 105                 110

Ala Ala Thr Ile Tyr His Trp Asp Leu Pro Gln Trp Ala Tyr Asp Lys
            115                 120                 125

Gly Gly Gly Trp Leu Asn Arg Glu Ser Ile Lys Trp Tyr Val Glu Tyr
        130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
```

```
              340                 345                 350
Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
        370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Leu Asp Asp Gly Ile Glu Asp
        435                 440                 445

<210> SEQ ID NO 9
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 9

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
```

-continued

```
                260                 265                 270
Phe Asp Phe Ile Lys Glu Gly Asp Leu Glu Thr Ile Ser Val Pro Ile
            275                 280                 285
Asp Phe Leu Gly Ile Asn Tyr Tyr Thr Arg Ser Ile Val Lys Tyr Asp
        290                 295                 300
Glu Asp Ser Met Leu Lys Ala Glu Asn Val Pro Gly Pro Gly Lys Arg
305                 310                 315                 320
Thr Glu Met Gly Trp Glu Ile Ser Pro Glu Ser Leu Tyr Asp Leu Leu
                325                 330                 335
Lys Arg Leu Asp Arg Glu Tyr Thr Lys Leu Pro Met Tyr Ile Thr Glu
            340                 345                 350
Asn Gly Ala Ala Phe Lys Asp Glu Val Thr Glu Asp Gly Arg Val His
        355                 360                 365
Asp Asp Glu Arg Ile Glu Tyr Ile Lys Glu His Leu Lys Ala Ala Ala
    370                 375                 380
Lys Phe Ile Gly Glu Gly Gly Asn Leu Lys Gly Tyr Phe Val Trp Ser
385                 390                 395                 400
Leu Met Asp Asn Phe Glu Trp Ala His Gly Tyr Ser Lys Arg Phe Gly
                405                 410                 415
Ile Val Tyr Val Asp Tyr Thr Thr Gln Lys Arg Ile Leu Lys Asp Ser
            420                 425                 430
Ala Leu Trp Tyr Lys Glu Val Ile Leu Asp Asp Gly Ile Glu Asp
        435                 440                 445

<210> SEQ ID NO 10
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 10

Met Ala Lys Phe Pro Arg Asp Phe Val Trp Gly Thr Ala Thr Ser Ser
1               5                   10                  15
Tyr Gln Ile Glu Gly Ala Val Asn Glu Asp Gly Arg Thr Pro Ser Ile
            20                  25                  30
Trp Asp Thr Phe Ser Lys Thr Glu Gly Lys Thr Tyr Lys Gly His Thr
        35                  40                  45
Gly Asp Val Ala Cys Asp His Tyr His Arg Tyr Lys Glu Asp Val Glu
    50                  55                  60
Ile Leu Lys Glu Ile Gly Val Lys Ala Tyr Arg Phe Ser Ile Ala Trp
65                  70                  75                  80
Pro Arg Ile Phe Pro Glu Glu Gly Lys Tyr Asn Pro Lys Gly Met Asp
                85                  90                  95
Phe Tyr Lys Lys Leu Ile Asp Glu Leu Gln Lys Arg Asp Ile Val Pro
            100                 105                 110
Ala Ala Thr Ile Tyr His Trp Asp Leu Pro Gln Trp Ala Tyr Asp Lys
        115                 120                 125
Gly Gly Gly Trp Leu Asn Arg Glu Ser Ile Lys Trp Tyr Val Glu Tyr
    130                 135                 140
Ala Thr Lys Leu Phe Glu Glu Leu Gly Asp Ala Ile Pro Leu Trp Ile
145                 150                 155                 160
Thr His Asn Glu Pro Trp Cys Ser Ser Ile Leu Ser Tyr Gly Ile Gly
                165                 170                 175
Glu His Ala Pro Gly His Lys Asn Tyr Arg Glu Ala Leu Ile Ala Ala
```

```
            180                 185                 190
His His Ile Leu Leu Ser His Gly Glu Ala Val Lys Ala Phe Arg Glu
        195                 200                 205
Met Asn Ile Lys Gly Ser Lys Ile Gly Ile Thr Leu Asn Leu Thr Pro
    210                 215                 220
Ala Tyr Pro Ala Ser Lys Glu Asp Lys Leu Ala Ala Gln Tyr
225                 230                 235                 240
Ala Asp Gly Phe Ala Asn Arg Trp Phe Leu Asp Pro Ile Phe Lys Gly
                245                 250                 255
Asn Tyr Pro Glu Asp Met Met Glu Leu Tyr Ser Lys Ile Ile Gly Glu
            260                 265                 270
Phe Asp Phe Ile Lys Glu Gly Asp Leu Glu Thr Ile Ser Val Pro Ile
        275                 280                 285
Asp Phe Leu Gly Val Asn Tyr Tyr Thr Arg Ser Ile Val Lys Tyr Asp
    290                 295                 300
Glu Asp Ser Met Leu Lys Ala Glu Asn Val Pro Gly Pro Gly Lys Arg
305                 310                 315                 320
Thr Glu Met Gly Trp Glu Ile Ser Pro Glu Ser Leu Tyr Asp Leu Leu
                325                 330                 335
Lys Arg Leu Asp Arg Glu Tyr Thr Lys Leu Pro Met Tyr Ile Thr Glu
            340                 345                 350
Asn Gly Ala Ala Phe Lys Asp Glu Val Thr Glu Asp Gly Arg Val His
        355                 360                 365
Asp Asp Glu Arg Ile Glu Tyr Ile Lys Glu His Leu Lys Ala Ala Ala
    370                 375                 380
Lys Phe Ile Gly Glu Gly Gly Asn Leu Lys Gly Tyr Phe Val Trp Ser
385                 390                 395                 400
Leu Met Asp Asn Phe Glu Trp Ala His Gly Tyr Ser Lys Arg Phe Gly
                405                 410                 415
Ile Val Tyr Val Asp Tyr Glu Thr Gln Lys Arg Ile Leu Lys Asp Ser
            420                 425                 430
Ala Leu Trp Tyr Lys Glu Val Ile Leu Asp Asp Gly Ile Glu Asp
        435                 440                 445

<210> SEQ ID NO 11
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 11

Met Ala Lys Phe Pro Arg Asp Phe Val Trp Gly Thr Ala Thr Ser Ser
1               5                   10                  15
Tyr Gln Ile Glu Gly Ala Val Asn Glu Asp Gly Arg Thr Pro Ser Ile
                20                  25                  30
Trp Asp Thr Phe Ser Lys Thr Glu Gly Lys Tyr Lys Gly His Thr
            35                  40                  45
Gly Asp Val Ala Cys Asp His Tyr His Arg Tyr Lys Glu Asp Val Glu
        50                  55                  60
Ile Leu Lys Glu Ile Gly Val Lys Ala Tyr Arg Phe Ser Ile Ala Trp
65                  70                  75                  80
Pro Arg Ile Phe Pro Glu Glu Gly Lys Tyr Asn Pro Lys Gly Met Asp
                85                  90                  95
Phe Tyr Lys Lys Leu Ile Asp Glu Leu Gln Lys Arg Asp Ile Val Pro
```

```
            100                 105                 110
Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
                180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
        210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 12
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 12

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
```

```
                20                  25                  30
Trp Asp Thr Phe Ser Lys Thr Pro Gly Lys Thr Tyr Lys Gly His Thr
            35                  40                  45
Gly Asp Val Ala Cys Asp His Tyr His Arg Tyr Lys Glu Asp Val Glu
        50                  55                  60
Ile Leu Lys Glu Ile Gly Val Lys Ala Tyr Arg Phe Ser Ile Ala Trp
65                  70                  75                  80
Pro Arg Ile Phe Pro Glu Glu Gly Lys Tyr Asn Pro Lys Gly Met Asp
                85                  90                  95
Phe Tyr Lys Lys Leu Ile Asp Glu Leu Gln Lys Arg Asp Ile Lys Pro
            100                 105                 110
Ala Ala Thr Ile Tyr His Trp Asp Leu Pro Gln Trp Ala Tyr Asp Lys
        115                 120                 125
Gly Gly Gly Trp Leu Asn Arg Glu Ser Ile Lys Trp Tyr Val Glu Tyr
    130                 135                 140
Ala Thr Lys Leu Phe Glu Glu Leu Gly Asp Ala Ile Pro Leu Trp Ile
145                 150                 155                 160
Thr His Asn Glu Pro Trp Cys Ser Ser Ile Leu Ser Tyr Gly Ile Gly
                165                 170                 175
Glu His Ala Pro Gly His Lys Asn Tyr Arg Glu Ala Leu Ile Ala Ala
            180                 185                 190
His His Ile Leu Leu Ser His Gly Glu Ala Val Lys Ala Phe Arg Glu
        195                 200                 205
Met Asn Ile Lys Gly Ser Lys Ile Gly Ile Thr Leu Asn Leu Thr Pro
    210                 215                 220
Ala Tyr Pro Ala Ser Glu Lys Glu Glu Asp Lys Leu Ala Ala Gln Tyr
225                 230                 235                 240
Ala Asp Gly Phe Ala Asn Arg Trp Phe Leu Asp Pro Ile Phe Lys Gly
                245                 250                 255
Asn Tyr Pro Glu Asp Met Met Glu Leu Tyr Ser Lys Ile Ile Gly Glu
            260                 265                 270
Phe Asp Phe Ile Lys Glu Gly Asp Leu Glu Thr Ile Ser Val Pro Ile
        275                 280                 285
Asp Phe Leu Gly Val Asn Tyr Tyr Thr Arg Ser Ile Val Lys Tyr Asp
    290                 295                 300
Glu Asp Ser Met Leu Lys Ala Glu Asn Val Pro Gly Pro Gly Lys Arg
305                 310                 315                 320
Thr Glu Met Gly Trp Glu Ile Ser Pro Glu Ser Leu Tyr Asp Leu Leu
                325                 330                 335
Lys Arg Leu Asp Arg Glu Tyr Thr Lys Leu Pro Met Tyr Ile Thr Glu
            340                 345                 350
Asn Gly Ala Ala Phe Lys Asp Glu Val Thr Glu Asp Gly Arg Val His
        355                 360                 365
Asp Asp Glu Arg Ile Glu Tyr Ile Lys Glu His Leu Lys Ala Ala Ala
    370                 375                 380
Lys Phe Ile Gly Glu Gly Gly Asn Leu Lys Gly Tyr Phe Val Trp Ser
385                 390                 395                 400
Leu Met Asp Asn Phe Glu Trp Ala His Gly Tyr Ser Lys Arg Phe Gly
                405                 410                 415
Ile Val Tyr Val Asp Tyr Thr Thr Gln Lys Arg Ile Leu Lys Asp Ser
            420                 425                 430
Ala Leu Trp Tyr Lys Glu Val Ile Leu Asp Asp Gly Ile Glu Asp
        435                 440                 445
```

```
<210> SEQ ID NO 13
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 13
```

| Met | Ala | Lys | Phe | Pro | Arg | Asp | Phe | Val | Trp | Gly | Thr | Ala | Thr | Ser | Ser |
|---|---|---|---|---|---|---|---|---|---|---|---|---|---|---|---|
| 1 | | | | 5 | | | | | 10 | | | | | 15 | |

| Tyr | Gln | Ile | Glu | Gly | Ala | Val | Asn | Glu | Asp | Gly | Arg | Thr | Pro | Ser | Ile |
| | | | 20 | | | | | 25 | | | | | 30 | | |

| Trp | Asp | Thr | Phe | Ser | Lys | Thr | Pro | Gly | Lys | Thr | Tyr | Lys | Gly | His | Thr |
| | | | 35 | | | | | 40 | | | | | 45 | | |

| Gly | Asp | Val | Ala | Cys | Asp | His | Tyr | His | Arg | Tyr | Lys | Glu | Asp | Val | Glu |
| | 50 | | | | | 55 | | | | | 60 | | | | |

| Ile | Leu | Lys | Glu | Ile | Gly | Val | Lys | Ala | Tyr | Arg | Phe | Ser | Ile | Ala | Trp |
| 65 | | | | | 70 | | | | | 75 | | | | | 80 |

| Pro | Arg | Ile | Phe | Pro | Glu | Glu | Gly | Lys | Tyr | Asn | Pro | Lys | Gly | Met | Asp |
| | | | | 85 | | | | | 90 | | | | | 95 | |

| Phe | Tyr | Lys | Lys | Leu | Ile | Asp | Glu | Leu | Gln | Lys | Arg | Asp | Ile | Val | Pro |
| | | | 100 | | | | | 105 | | | | | 110 | | |

| Ala | Ala | Thr | Ile | Tyr | His | Trp | Asp | Leu | Pro | Gln | Trp | Ala | Tyr | Asp | Lys |
| | | | 115 | | | | | 120 | | | | | 125 | | |

| Gly | Gly | Gly | Trp | Leu | Asn | Arg | Glu | Ser | Ile | Lys | Trp | Tyr | Val | Glu | Tyr |
| | 130 | | | | | 135 | | | | | 140 | | | | |

| Ala | Thr | Lys | Leu | Phe | Glu | Glu | Leu | Gly | Asp | Ala | Ile | Pro | Leu | Trp | Ile |
| 145 | | | | | 150 | | | | | 155 | | | | | 160 |

| Thr | His | Asn | Glu | Pro | Trp | Cys | Ser | Ser | Ile | Leu | Ser | Tyr | Gly | Ile | Gly |
| | | | | 165 | | | | | 170 | | | | | 175 | |

| Glu | His | Ala | Pro | Gly | His | Lys | Asn | Tyr | Arg | Glu | Ala | Leu | Ile | Ala | Ala |
| | | | 180 | | | | | 185 | | | | | 190 | | |

| His | His | Ile | Leu | Leu | Ser | His | Gly | Glu | Ala | Val | Lys | Ala | Phe | Arg | Glu |
| | | | 195 | | | | | 200 | | | | | 205 | | |

| Met | Asn | Ile | Lys | Gly | Ser | Lys | Ile | Gly | Ile | Thr | Leu | Asn | Leu | Thr | Pro |
| | 210 | | | | | 215 | | | | | 220 | | | | |

| Ala | Tyr | Pro | Ala | Ser | Glu | Lys | Glu | Glu | Asp | Lys | Leu | Ala | Ala | Gln | Tyr |
| 225 | | | | | 230 | | | | | 235 | | | | | 240 |

| Ala | Asp | Gly | Phe | Ala | Asn | Arg | Trp | Phe | Leu | Asp | Pro | Ile | Phe | Lys | Gly |
| | | | | 245 | | | | | 250 | | | | | 255 | |

| Asn | Tyr | Pro | Glu | Asp | Met | Met | Glu | Leu | Tyr | Ser | Lys | Ile | Ile | Gly | Glu |
| | | | 260 | | | | | 265 | | | | | 270 | | |

| Phe | Asp | Phe | Ile | Lys | Glu | Gly | Asp | Leu | Glu | Thr | Ile | Ser | Val | Pro | Ile |
| | | | 275 | | | | | 280 | | | | | 285 | | |

| Asp | Phe | Leu | Gly | Ile | Asn | Tyr | Tyr | Thr | Arg | Ser | Ile | Val | Lys | Tyr | Asp |
| | 290 | | | | | 295 | | | | | 300 | | | | |

| Glu | Asp | Ser | Met | Leu | Lys | Ala | Glu | Asn | Val | Pro | Gly | Pro | Gly | Lys | Arg |
| 305 | | | | | 310 | | | | | 315 | | | | | 320 |

| Thr | Glu | Met | Gly | Trp | Glu | Ile | Ser | Pro | Glu | Ser | Leu | Tyr | Asp | Leu | Leu |
| | | | | 325 | | | | | 330 | | | | | 335 | |

| Lys | Arg | Leu | Asp | Arg | Glu | Tyr | Thr | Lys | Leu | Pro | Met | Tyr | Ile | Thr | Glu |
| | | | 340 | | | | | 345 | | | | | 350 | | |

| Asn | Gly | Ala | Ala | Phe | Lys | Asp | Glu | Val | Thr | Glu | Asp | Gly | Arg | Val | His |
| | | | 355 | | | | | 360 | | | | | 365 | | |

```
Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Leu Asp Asp Gly Ile Glu Asp
        435                 440                 445
```

<210> SEQ ID NO 14
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 14

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285
```

```
Asp Phe Leu Gly Val Asn Tyr Tyr Thr Arg Ser Ile Val Lys Tyr Asp
        290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                    325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                    405                 410                 415

Ile Val Tyr Val Asp Tyr Glu Thr Gln Lys Arg Ile Leu Lys Asp Ser
                420                 425                 430

Ala Leu Trp Tyr Lys Glu Val Ile Leu Asp Asp Gly Ile Glu Asp
            435                 440                 445

<210> SEQ ID NO 15
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 15

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205
```

```
Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 16
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 16

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125
```

Gly Gly Gly Trp Leu Asn Arg Glu Ser Ile Lys Trp Tyr Val Glu Tyr
130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
                180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
            275                 280                 285

Asp Phe Leu Gly Ile Asn Tyr Tyr Thr Arg Ser Ile Val Lys Tyr Asp
290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Leu Asp Asp Gly Ile Glu Asp
435                 440                 445

<210> SEQ ID NO 17
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 17

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
                20                  25                  30

Trp Asp Thr Phe Ser Lys Thr Glu Gly Lys Thr Tyr Lys Gly His Thr
            35                  40                  45

Gly Asp Val Ala Cys Asp His Tyr His Arg Tyr Lys Glu Asp Val Glu
 50                  55                  60

Ile Leu Lys Glu Ile Gly Val Lys Ala Tyr Arg Phe Ser Ile Ala Trp
 65                  70                  75                  80

Pro Arg Ile Phe Pro Glu Glu Gly Lys Tyr Asn Pro Lys Gly Met Asp
                 85                  90                  95

Phe Tyr Lys Lys Leu Ile Asp Glu Leu Gln Lys Arg Asp Ile Lys Pro
             100                 105                 110

Ala Ala Thr Ile Tyr His Trp Asp Leu Pro Gln Trp Ala Tyr Asp Lys
             115                 120                 125

Gly Gly Gly Trp Leu Asn Arg Glu Ser Ile Lys Trp Tyr Val Glu Tyr
 130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                 165                 170                 175

Glu His Ala Pro Gly His Lys Asn Tyr Arg Glu Ala Leu Ile Ala Ala
             180                 185                 190

His His Ile Leu Leu Ser His Gly Glu Ala Val Lys Ala Phe Arg Glu
 195                 200                 205

Met Asn Ile Lys Gly Ser Lys Ile Gly Ile Thr Leu Asn Leu Thr Pro
 210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                 245                 250                 255

Asn Tyr Pro Glu Asp Met Met Glu Leu Tyr Ser Lys Ile Ile Gly Glu
             260                 265                 270

Phe Asp Phe Ile Lys Glu Gly Asp Leu Glu Thr Ile Ser Val Pro Ile
 275                 280                 285

Asp Phe Leu Gly Val Asn Tyr Tyr Thr Arg Ser Ile Val Lys Tyr Asp
 290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                 325                 330                 335

Lys Arg Leu Asp Arg Glu Tyr Thr Lys Leu Pro Met Tyr Ile Thr Glu
             340                 345                 350

Asn Gly Ala Ala Phe Lys Asp Glu Val Thr Glu Asp Gly Arg Val His
             355                 360                 365

Asp Asp Glu Arg Ile Glu Tyr Ile Lys Glu His Leu Lys Ala Ala Ala
 370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                 405                 410                 415

Ile Val Tyr Val Asp Tyr Glu Thr Gln Lys Arg Ile Leu Lys Asp Ser
             420                 425                 430

Ala Leu Trp Tyr Lys Glu Val Ile Leu Asp Asp Gly Ile Glu Asp
             435                 440                 445

<210> SEQ ID NO 18
<211> LENGTH: 447

<212> TYPE: PRT
<213> ORGANISM: Artificial Sequence
<220> FEATURE:
<223> OTHER INFORMATION: Synthetic Polypeptide

<400> SEQUENCE: 18

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380
```

```
Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
            405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 19
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 19

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Gly Lys Tyr Asn Pro Lys Gly Met Asp
            85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
            165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
            245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300
```

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
            325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
            405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Leu Asp Asp Gly Ile Glu Asp
            435                 440                 445

<210> SEQ ID NO 20
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 20

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
            85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
            115                 120                 125

Gly Gly Gly Trp Leu Asn Arg Glu Ser Ile Lys Trp Tyr Val Glu Tyr
130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
            165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
            245                 250                 255

Asn Tyr Pro Glu Asp Met Met Glu Leu Tyr Ser Lys Ile Ile Gly Glu
        260                 265                 270

Phe Asp Phe Ile Lys Glu Gly Asp Leu Glu Thr Ile Ser Val Pro Ile
    275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 21
<211> LENGTH: 447
<212> TYPE: PRT
<213> ORGANISM: Artificial Sequence
<220> FEATURE:
<223> OTHER INFORMATION: Synthetic Poylpeptide

<400> SEQUENCE: 21

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Gly Lys Tyr Asn Pro Lys Gly Met Asp
            85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
            165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
            245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
            325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
            405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 22
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 22

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

```
Ile Leu Lys Glu Ile Gly Val Lys Ala Tyr Arg Phe Ser Ile Ala Trp
 65                  70                  75                  80

Pro Arg Ile Phe Pro Glu Glu Gly Lys Tyr Asn Pro Lys Gly Met Asp
                 85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Leu Asp Asp Gly Ile Glu Asp
        435                 440                 445

<210> SEQ ID NO 23
<211> LENGTH: 447
<212> TYPE: PRT
<213> ORGANISM: Artificial Sequence
<220> FEATURE:
<223> OTHER INFORMATION: Synthetic Polypeptide
```

<400> SEQUENCE: 23

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65              70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
```

405                 410                 415
Ile Val Tyr Val Asp Tyr Glu Thr Gln Lys Arg Ile Leu Lys Asp Ser
                420                 425                 430

Ala Leu Trp Tyr Lys Glu Val Ile Leu Asp Asp Gly Ile Glu Asp
        435                 440                 445

<210> SEQ ID NO 24
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 24

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu

```
            325                 330                 335
Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
            370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
                420                 425                 430

Ala Leu Trp Tyr Lys Glu Val Ile Arg Asp Asp Gly Ile Glu Asp
                435                 440                 445

<210> SEQ ID NO 25
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 25

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
```

```
                        245                 250                 255
Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
            275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
                355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                    405                 410                 415

Ile Val Tyr Val Asp Tyr Glu Thr Gln Lys Arg Ile Leu Lys Asp Ser
                420                 425                 430

Ala Leu Trp Tyr Lys Glu Val Ile Leu Asp Asp Gly Ile Glu Asp
                435                 440                 445
```

<210> SEQ ID NO 26
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 26

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
```

```
                       165                 170                 175
Glu His Ala Pro Gly His Lys Asn Tyr Arg Glu Ala Leu Ile Ala Ala
                180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 27
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 27

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
```

85                  90                  95
Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Val Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 28
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 28

Met Ala Lys Phe Pro Arg Asp Phe Val Trp Gly Thr Ala Thr Ser Ser

-continued

```
1               5                   10                  15
Tyr Gln Ile Glu Gly Ala Val Asn Glu Asp Gly Arg Thr Pro Ser Ile
                20                  25                  30
Trp Asp Thr Phe Ser Lys Thr Glu Gly Lys Thr Tyr Lys Gly His Thr
                35                  40                  45
Gly Asp Val Ala Cys Asp His Tyr Arg Tyr Lys Glu Asp Val Glu
                50                  55                  60
Ile Leu Lys Glu Ile Gly Val Lys Ala Tyr Arg Phe Ser Ile Ala Trp
65                  70                  75                  80
Pro Arg Ile Phe Pro Glu Gly Lys Tyr Asn Pro Lys Gly Met Asp
                85                  90                  95
Phe Tyr Lys Lys Leu Ile Asp Glu Leu Gln Lys Arg Asp Ile Lys Pro
                100                 105                 110
Ala Ala Thr Ile Tyr His Trp Asp Leu Pro Gln Trp Ala Tyr Asp Lys
                115                 120                 125
Gly Gly Gly Trp Leu Asn Arg Glu Ser Ile Lys Trp Tyr Val Glu Tyr
                130                 135                 140
Ala Thr Lys Leu Phe Glu Glu Leu Gly Asp Ala Ile Pro Leu Trp Ile
145                 150                 155                 160
Thr His Asn Glu Pro Trp Cys Ser Ser Ile Leu Ser Tyr Gly Ile Gly
                165                 170                 175
Glu His Ala Pro Gly His Lys Asn Tyr Arg Glu Ala Leu Ile Ala Ala
                180                 185                 190
His His Ile Leu Leu Ser His Gly Glu Ala Val Lys Ala Phe Arg Glu
                195                 200                 205
Met Asn Ile Lys Gly Ser Lys Ile Gly Ile Thr Leu Asn Leu Thr Pro
                210                 215                 220
Ala Tyr Pro Ala Ser Glu Lys Glu Asp Lys Leu Ala Ala Gln Tyr
225                 230                 235                 240
Ala Asp Gly Phe Ala Asn Arg Trp Phe Leu Asp Pro Ile Phe Lys Gly
                245                 250                 255
Asn Tyr Pro Glu Asp Met Met Glu Leu Tyr Ser Lys Ile Ile Gly Glu
                260                 265                 270
Phe Asp Phe Ile Lys Glu Gly Asp Leu Glu Thr Ile Ser Val Pro Ile
                275                 280                 285
Asp Phe Leu Gly Ile Asn Tyr Tyr Thr Arg Ser Ile Val Lys Tyr Asp
                290                 295                 300
Glu Asp Ser Met Leu Lys Ala Glu Asn Val Pro Gly Pro Gly Lys Arg
305                 310                 315                 320
Thr Glu Met Gly Trp Glu Ile Ser Pro Glu Ser Leu Tyr Asp Leu Leu
                325                 330                 335
Lys Arg Leu Asp Arg Glu Tyr Thr Lys Leu Pro Met Tyr Ile Thr Glu
                340                 345                 350
Asn Gly Ala Ala Phe Lys Asp Glu Val Thr Glu Asp Gly Arg Val His
                355                 360                 365
Asp Asp Glu Arg Ile Glu Tyr Ile Lys Glu His Leu Lys Ala Ala Ala
                370                 375                 380
Lys Phe Ile Gly Glu Gly Gly Asn Leu Lys Gly Tyr Phe Val Trp Ser
385                 390                 395                 400
Leu Met Asp Asn Phe Glu Trp Ala His Gly Tyr Ser Lys Arg Phe Gly
                405                 410                 415
Ile Val Tyr Val Asp Tyr Glu Thr Gln Lys Arg Ile Leu Lys Asp Ser
                420                 425                 430
```

```
Ala Leu Trp Tyr Lys Glu Val Ile Leu Asp Asp Gly Ile Glu Asp
        435                 440                 445

<210> SEQ ID NO 29
<211> LENGTH: 447
<212> TYPE: PRT
<213> ORGANISM: Artificial Sequence
<220> FEATURE:
<223> OTHER INFORMATION: Synthetic Poylpeptide

<400> SEQUENCE: 29

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350
```

```
Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 30
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 30

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270
```

```
Phe Asp Phe Ile Lys Glu Gly Asp Leu Glu Thr Ile Ser Val Pro Ile
            275                 280                 285

Asp Phe Leu Gly Val Asn Tyr Tyr Thr Arg Ser Ile Val Lys Tyr Asp
        290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Arg Asp Asp Gly Ile Glu Asp
            435                 440                 445

<210> SEQ ID NO 31
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 31

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190
```

```
His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
        290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
                355                 360                 365

Asp Asp Glu Arg Ile Glu Tyr Ile Lys Glu His Leu Lys Ala Ala
        370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
                420                 425                 430

Ala Leu Trp Tyr Lys Glu Val Ile Arg Asp Asp Gly Ile Glu Asp
        435                 440                 445

<210> SEQ ID NO 32
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 32

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
                20                  25                  30

Trp Asp Thr Phe Ser Lys Thr Pro Gly Lys Thr Tyr Lys Gly His Thr
            35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110
```

```
Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Leu Asp Asp Gly Ile Glu Asp
        435                 440                 445

<210> SEQ ID NO 33
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 33

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30
```

```
Trp Asp Thr Phe Ser Lys Thr Pro Gly Lys Thr Tyr Lys Gly His Thr
            35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
            115                 120                 125

Gly Gly Gly Trp Leu Asn Arg Glu Ser Ile Lys Trp Tyr Val Glu Tyr
            130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
            210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
            275                 280                 285

Asp Phe Leu Gly Ile Asn Tyr Tyr Thr Arg Ser Ile Val Lys Tyr Asp
            290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
            370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Thr Thr Gln Lys Arg Ile Leu Lys Asp Ser
            420                 425                 430

Ala Leu Trp Tyr Lys Glu Val Ile Arg Asp Asp Gly Ile Glu Asp
            435                 440                 445
```

<210> SEQ ID NO 34
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 34

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
                20                  25                  30

Trp Asp Thr Phe Ser Lys Thr Pro Gly Lys Thr Tyr Lys Gly His Thr
            35                  40                  45

Gly Asp Val Ala Cys Asp His Tyr His Arg Tyr Lys Glu Asp Val Glu
        50                  55                  60

Ile Leu Lys Glu Ile Gly Val Lys Ala Tyr Arg Phe Ser Ile Ala Trp
65                  70                  75                  80

Pro Arg Ile Phe Pro Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
                100                 105                 110

Ala Ala Thr Ile Tyr His Trp Asp Leu Pro Gln Trp Ala Tyr Asp Lys
            115                 120                 125

Gly Gly Gly Trp Leu Asn Arg Glu Ser Ile Lys Trp Tyr Val Glu Tyr
        130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
                180                 185                 190

His His Ile Leu Leu Ser His Gly Glu Ala Val Lys Ala Phe Arg Glu
            195                 200                 205

Met Asn Ile Lys Gly Ser Lys Ile Gly Ile Thr Leu Asn Leu Thr Pro
        210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
                260                 265                 270

Phe Asp Phe Ile Lys Glu Gly Asp Leu Glu Thr Ile Ser Val Pro Ile
            275                 280                 285

Asp Phe Leu Gly Val Asn Tyr Tyr Thr Arg Ser Ile Val Lys Tyr Asp
        290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
            355                 360                 365
```

```
Asp Asp Glu Arg Ile Glu Tyr Ile Lys Glu His Leu Lys Ala Ala Ala
    370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
                420                 425                 430

Ala Leu Trp Tyr Lys Glu Val Ile Arg Asp Asp Gly Ile Glu Asp
            435                 440                 445

<210> SEQ ID NO 35
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 35

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Val Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
    210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285
```

Asp Phe Leu Gly Ile Asn Tyr Tyr Thr Arg Ser Ile Val Lys Tyr Asp
    290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
                340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
                420                 425                 430

Ala Leu Trp Tyr Lys Glu Val Ile Arg Asp Asp Gly Ile Glu Asp
            435                 440                 445

<210> SEQ ID NO 36
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 36

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
                20                  25                  30

Trp Asp Thr Phe Ser Lys Thr Glu Gly Lys Thr Tyr Lys Gly His Thr
            35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
                85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125

Gly Gly Gly Trp Leu Asn Arg Glu Ser Ile Lys Trp Tyr Val Glu Tyr
    130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

```
Met Asn Ile Lys Gly Ser Lys Ile Gly Ile Thr Leu Asn Leu Thr Pro
210                 215                 220

Ala Tyr Pro Ala Ser Glu Lys Glu Glu Asp Lys Leu Ala Ala Gln Tyr
225                 230                 235                 240

Ala Asp Gly Phe Ala Asn Arg Trp Phe Leu Asp Pro Ile Phe Lys Gly
            245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
            325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
            355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
            405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Arg Asp Asp Gly Ile Glu Asp
            435                 440                 445

<210> SEQ ID NO 37
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 37

Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Pro Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
            85                  90                  95

Phe Tyr Lys Lys Leu Ile Asp Glu Leu Gln Lys Arg Asp Ile Lys Pro
            100                 105                 110

Ala Ala Thr Ile Tyr His Trp Asp Leu Pro Gln Trp Ala Tyr Asp Lys
        115                 120                 125
```

Gly Gly Gly Trp Leu Asn Arg Glu Ser Ile Lys Trp Tyr Val Glu Tyr
            130                 135                 140

Ala Thr Lys Leu Phe Glu Glu Leu Gly Asp Ala Ile Pro Leu Trp Ile
145                 150                 155                 160

Thr His Asn Glu Pro Trp Cys Ser Ser Ile Leu Ser Tyr Gly Ile Gly
                165                 170                 175

Glu His Ala Pro Gly His Lys Asn Tyr Arg Glu Ala Leu Ile Ala Ala
            180                 185                 190

His His Ile Leu Leu Ser His Gly Glu Ala Val Lys Ala Phe Arg Glu
        195                 200                 205

Met Asn Ile Lys Gly Ser Lys Ile Gly Ile Thr Leu Asn Leu Thr Pro
210                 215                 220

Ala Tyr Pro Ala Ser Glu Lys Glu Asp Lys Leu Ala Ala Gln Tyr
225                 230                 235                 240

Ala Asp Gly Phe Ala Asn Arg Trp Phe Leu Asp Pro Ile Phe Lys Gly
                245                 250                 255

Asn Tyr Pro Glu Asp Met Met Glu Leu Tyr Ser Lys Ile Ile Gly Glu
            260                 265                 270

Phe Asp Phe Ile Lys Glu Gly Asp Leu Glu Thr Ile Ser Val Pro Ile
        275                 280                 285

Asp Phe Leu Gly Ile Asn Tyr Tyr Thr Arg Ser Ile Val Lys Tyr Asp
290                 295                 300

Glu Asp Ser Met Leu Lys Ala Glu Asn Val Pro Gly Pro Gly Lys Arg
305                 310                 315                 320

Thr Glu Met Gly Trp Glu Ile Ser Pro Glu Ser Leu Tyr Asp Leu Leu
                325                 330                 335

Lys Arg Leu Asp Arg Glu Tyr Thr Lys Leu Pro Met Tyr Ile Thr Glu
            340                 345                 350

Asn Gly Ala Ala Phe Lys Asp Glu Val Thr Glu Asp Gly Arg Val His
        355                 360                 365

Asp Asp Glu Arg Ile Glu Tyr Ile Lys Glu His Leu Lys Ala Ala Ala
370                 375                 380

Lys Phe Ile Gly Glu Gly Gly Asn Leu Lys Gly Tyr Phe Val Trp Ser
385                 390                 395                 400

Leu Met Asp Asn Phe Glu Trp Ala His Gly Tyr Ser Lys Arg Phe Gly
                405                 410                 415

Ile Val Tyr Val Asp Tyr Glu Thr Gln Lys Arg Ile Leu Lys Asp Ser
            420                 425                 430

Ala Leu Trp Tyr Lys Glu Val Ile Arg Asp Asp Gly Ile Glu Asp
        435                 440                 445

<210> SEQ ID NO 38
<211> LENGTH: 1341
<212> TYPE: DNA
<213> ORGANISM: Artificial Sequence
<220> FEATURE:
<223> OTHER INFORMATION: Synthetic Polynucleotide

<400> SEQUENCE: 38
atggccaagt tcctcgcga ctttgtatgg ggtacagcca catcgagtta tcagattgaa     60
ggcgcggtga atgaagatgg tcgtacaccg tctatctggg acaccttttc gaaaaccgag    120
ggcaaaacct ataaggcca tacgggtgat gttgcctgtg atcactatca ccgctataag    180
gaagatgtgg aaattctgaa agaaattgga gtcaaagcct accggtttag cattgcatgg    240
ccacgtatct ttcctgagga aggcaaatac aacccgaaag gtatggattt ctacaagaaa    300

```
ctcattgacg aactgcaaaa gcgcgatatt gttcccgcag cgaccattta tcactgggat      360
ctgccacaat gggcctatga caaaggcggt ggctggctga accgtgagtc catcaaatgg      420
tatgtggagt acgcgaccaa attgtttgaa gaactgggtg atgcgatccc gctgtggatt      480
acccataatg agccatggtg ctcttctatc ctcagttatg gtatcggcga acatgcacct      540
ggtcataaga actatcgcga agcgcttatt gctgcgcatc acatcctgct ctcacatggc      600
gaagcggtca aagcgtttcg cgaaatgaac attaagggga gcaaaatcgg cattacgctt      660
aacttgactc cggcgtatcc agcaagtgag aaagaagaag ataaactggc tgcacagtat      720
gcagatggct ttgccaatcg ctggttcctt gacccgatct tcaagggtaa ctatccggag      780
gacatgatgg aattgtacag caaaattatt ggggaattcg atttcattaa ggaaggcgat      840
ctggagacta tcagcgtccc gattgacttc ttaggcgtca attactacac tcggagcatt      900
gttaaatacg atgaagattc catgctgaaa gcagagaacg taccgggacc gggtaaacgt      960
accgaaatgg ggtgggaaat ctcgcccgag tcactgtacg acttactgaa acgcttagac    1020
cgtgagtata cgaaactgcc gatgtatatc accgaaaatg gagctgcgtt taaagatgaa    1080
gtaacggaag atggtcgtgt tcacgacgat gaacgcatcg aatacatcaa agagcacctg    1140
aaagctgccg ctaaatttat cggggaaggc ggtaatctga aggatactt tgtgtggtca    1200 ttaatggaca acttcgaatg ggcgcatggc tactccaaac gtttcggcat tgtgtatgtg    1260
gactatacga cccagaaacg cattctgaag gatagcgcct tgtggtacaa agaggtgatt    1320
ctggatgatg ggattgaaga t                                               1341

<210> SEQ ID NO 39
<211> LENGTH: 1341
<212> TYPE: DNA
<213> ORGANISM: Artificial Sequence
<220> FEATURE:
<223> OTHER INFORMATION: Synthetic Polynucleotide

<400> SEQUENCE: 39
atggccaagt ttcctcgcga ctttgtatgg ggtacagcca catcgagtta tcagattgaa       60
ggcgcggtga atgaagatgg tcgtacaccg tctatctggg acaccttttc gaaaaccccg      120
ggcaaaacct ataaaggcca tacgggtgat gttgcctgtg atcactatca ccgctataag      180
gaagatgtgg aaattctgaa agaaattgga gtcaaagcct accggtttag cattgcatgg      240
ccacgtatct ttcctgagga aggcaaatac aacccgaaag gtatggattt ctacaagaaa      300
ctcattgacg aactgcaaaa gcgcgatatt gttcccgcag cgaccattta tcactgggat      360
ctgccacaat gggcctatga caaaggcggt ggctggctga accgtgagtc catcaaatgg      420
tatgtggagt acgcgaccaa attgtttgaa gaactgggtg atgcgatccc gctgtggatt      480
acccataatg agccatggtg ctcttctatc ctcagttatg gtatcggcga acatgcacct      540
ggtcataaga actatcgcga agcgcttatt gctgcgcatc acatcctgct ctcacatggc      600
gaagcggtca aagcgtttcg cgaaatgaac attaagggga gcaaaatcgg cattacgctt      660
aacttgactc cggcgtatcc agcaagtgag aaagaagaag ataaactggc tgcacagtat      720
gcagatggct ttgccaatcg ctggttcctt gacccgatct tcaagggtaa ctatccggag      780
gacatgatgg aattgtacag caaaattatt ggggaattcg atttcattaa ggaaggcgat      840
ctggagacta tcagcgtccc gattgacttc ttaggcgtca attactacac tcggagcatt      900
gttaaatacg atgaagattc catgctgaaa gcagagaacg taccgggacc gggtaaacgt      960
```

```
accgaaatgg ggtgggaaat ctcgcccgag tcactgtacg acttactgaa acgcttagac    1020
cgtgagtata cgaaactgcc gatgtatatc accgaaaatg gagctgcgtt taaagatgaa    1080
gtaacggaag atggtcgtgt tcacgacgat gaacgcatcg aatacatcaa agagcacctg    1140
aaagctgccg ctaaatttat cggggaaggc ggtaatctga aaggatactt tgtgtggtca    1200
ttaatggaca acttcgaatg ggcgcatggc tactccaaac gtttcggcat tgtgtatgtg    1260
gactatacga cccagaaacg cattctgaag gatagcgcct tgtggtacaa agaggtgatt    1320
ctggatgatg ggattgaaga t                                             1341

<210> SEQ ID NO 40
<211> LENGTH: 1341
<212> TYPE: DNA
<213> ORGANISM: Artificial Sequence
<220> FEATURE:
<223> OTHER INFORMATION: Synthetic Polynucleotide

<400> SEQUENCE: 40
atggccaagt ttcctcgcga ctttgtatgg ggtacagcca catcgagtta tcagattgaa      60
ggcgcggtga atgaagatgg tcgtacaccg tctatctggg acaccttttc gaaaaccgag     120
ggcaaaacct ataaaggcca tacgggtgat gttgcctgtg atcactatca ccgctataag     180
gaagatgtgg aaattctgaa agaaattgga gtcaaagcct accggtttag cattgcatgg     240
ccacgtatct ttcctgagga aggcaaatac aacccgaaag gtatggattt ctacaagaaa     300
ctcattgacg aactgcaaaa gcgcgatatt aaacccgcag cgaccattta tcactgggat     360
ctgccacaat gggcctatga caaaggcggt ggctggctga accgtgagtc catcaaatgg     420
tatgtggagt acgcgaccaa attgtttgaa gaactgggtg atgcgatccc gctgtggatt     480
acccataatg agccatggtg ctcttctatc ctcagttatg gtatcggcga acatgcacct     540
ggtcataaga actatcgcga agcgcttatt gctgcgcatc acatcctgct ctcacatggc     600
gaagcggtca aagcgtttcg cgaaatgaac attaagggga gcaaaatcgg cattacgctt     660
aacttgactc cggcgtatcc agcaagtgag aaagaagaag ataaactggc tgcacagtat     720
gcagatggct tgccaatcg ctggttcctt gacccgatct tcaagggtaa ctatccggag     780
gacatgatgg aattgtacag caaaattatt ggggaattcg atttcattaa ggaaggcgat     840
ctggagacta tcagcgtccc gattgacttc ttaggcgtca attactacac tcggagcatt     900
gttaaatacg atgaagattc catgctgaaa gcagagaacg taccgggacc gggtaaacgt     960
accgaaatgg ggtgggaaat ctcgcccgag tcactgtacg acttactgaa acgcttagac    1020
cgtgagtata cgaaactgcc gatgtatatc accgaaaatg gagctgcgtt taaagatgaa    1080
gtaacggaag atggtcgtgt tcacgacgat gaacgcatcg aatacatcaa agagcacctg    1140
aaagctgccg ctaaatttat cggggaaggc ggtaatctga aaggatactt tgtgtggtca    1200
ttaatggaca acttcgaatg ggcgcatggc tactccaaac gtttcggcat tgtgtatgtg    1260
gactatacga cccagaaacg cattctgaag gatagcgcct tgtggtacaa agaggtgatt    1320
ctggatgatg ggattgaaga t                                             1341

<210> SEQ ID NO 41
<211> LENGTH: 1341
<212> TYPE: PRT
<213> ORGANISM: Artificial Sequence
<220> FEATURE:
<223> OTHER INFORMATION: Synthetic Polynucleotide

<400> SEQUENCE: 41
```

-continued

```
Ala Thr Gly Gly Cys Cys Ala Ala Gly Thr Thr Thr Cys Cys Thr Cys
1               5                   10                  15

Gly Cys Gly Ala Cys Thr Thr Thr Gly Thr Ala Thr Gly Gly Gly Gly
            20                  25                  30

Thr Ala Cys Ala Gly Cys Cys Ala Cys Ala Thr Cys Gly Ala Gly Thr
        35                  40                  45

Thr Ala Thr Cys Ala Gly Ala Thr Thr Gly Ala Ala Gly Gly Cys Gly
    50                  55                  60

Cys Gly Gly Thr Gly Ala Ala Thr Gly Ala Ala Gly Ala Thr Gly Gly
65                  70                  75                  80

Thr Cys Gly Thr Ala Cys Ala Cys Cys Gly Thr Cys Thr Ala Thr Cys
                85                  90                  95

Thr Gly Gly Gly Ala Cys Ala Cys Cys Thr Thr Thr Thr Cys Gly Ala
            100                 105                 110

Ala Ala Ala Cys Cys Gly Ala Gly Gly Gly Cys Ala Ala Ala Ala Cys
        115                 120                 125

Cys Thr Ala Thr Ala Ala Ala Gly Gly Cys Cys Ala Thr Ala Cys Gly
    130                 135                 140

Gly Gly Thr Gly Ala Thr Gly Thr Thr Gly Cys Cys Thr Gly Thr Gly
145                 150                 155                 160

Ala Thr Cys Ala Cys Thr Ala Thr Cys Ala Cys Cys Gly Cys Thr Ala
                165                 170                 175

Thr Ala Ala Gly Gly Ala Ala Gly Ala Thr Gly Thr Gly Gly Ala Ala
            180                 185                 190

Ala Thr Thr Cys Thr Gly Ala Ala Ala Gly Ala Ala Ala Thr Thr Gly
        195                 200                 205

Gly Ala Gly Thr Cys Ala Ala Ala Gly Cys Cys Thr Ala Cys Cys Gly
    210                 215                 220

Gly Thr Thr Thr Ala Gly Cys Ala Thr Thr Gly Cys Ala Thr Gly Gly
225                 230                 235                 240

Cys Cys Ala Cys Gly Thr Ala Thr Cys Thr Thr Thr Cys Cys Thr Gly
                245                 250                 255

Ala Gly Gly Ala Ala Gly Gly Cys Ala Ala Ala Thr Ala Cys Ala Ala
            260                 265                 270

Cys Cys Cys Gly Ala Ala Ala Gly Gly Thr Ala Thr Gly Gly Ala Thr
        275                 280                 285

Thr Thr Cys Thr Ala Cys Ala Ala Gly Ala Ala Ala Cys Thr Cys Ala
    290                 295                 300

Thr Thr Gly Ala Cys Gly Ala Ala Cys Thr Gly Cys Ala Ala Ala Ala
305                 310                 315                 320

Gly Cys Gly Cys Gly Ala Thr Ala Thr Thr Gly Thr Thr Cys Cys Cys
                325                 330                 335

Gly Cys Ala Gly Cys Gly Ala Cys Cys Ala Thr Thr Thr Ala Thr Cys
            340                 345                 350

Ala Cys Thr Gly Gly Gly Ala Thr Cys Thr Gly Cys Cys Ala Cys Ala
        355                 360                 365

Ala Thr Gly Gly Gly Cys Cys Thr Ala Thr Gly Ala Cys Ala Ala Ala
    370                 375                 380

Gly Gly Cys Gly Gly Thr Gly Gly Cys Thr Gly Gly Cys Thr Gly Ala
385                 390                 395                 400

Ala Cys Cys Gly Thr Gly Ala Gly Thr Cys Cys Ala Thr Cys Ala Ala
                405                 410                 415
```

Ala Thr Gly Gly Thr Ala Thr Gly Gly Ala Gly Thr Ala Cys
    420             425             430

Gly Cys Gly Ala Cys Cys Ala Ala Ala Thr Gly Thr Thr Gly
        435             440             445

Ala Ala Gly Ala Ala Cys Thr Gly Gly Thr Gly Ala Thr Gly Cys
450                 455             460

Gly Ala Thr Cys Cys Cys Gly Cys Thr Gly Thr Gly Ala Thr Thr
465             470             475             480

Ala Cys Cys Cys Ala Thr Ala Ala Gly Ala Gly Cys Cys Ala Thr
                485             490             495

Gly Gly Thr Gly Cys Thr Cys Thr Thr Cys Thr Ala Thr Cys Cys Thr
            500             505             510

Cys Ala Gly Thr Thr Ala Thr Gly Gly Thr Ala Thr Cys Gly Gly Cys
            515             520             525

Gly Ala Ala Cys Ala Thr Gly Cys Ala Cys Cys Thr Gly Gly Thr Cys
            530             535             540

Ala Thr Ala Ala Gly Ala Ala Cys Thr Ala Thr Cys Gly Cys Gly Ala
545                 550             555             560

Ala Gly Cys Gly Cys Thr Thr Ala Thr Gly Cys Thr Gly Cys Gly
            565             570             575

Cys Ala Thr Cys Ala Cys Ala Thr Cys Cys Thr Gly Cys Thr Cys Thr
            580             585             590

Cys Ala Cys Ala Thr Gly Cys Gly Ala Ala Gly Cys Gly Gly Thr
            595             600             605

Cys Ala Ala Ala Gly Cys Gly Thr Thr Thr Cys Gly Cys Gly Ala Ala
610                 615             620

Ala Thr Gly Ala Ala Cys Ala Thr Thr Ala Gly Gly Gly Gly Ala
625                 630             635             640

Gly Cys Ala Ala Ala Ala Thr Cys Gly Gly Cys Ala Thr Thr Ala Cys
            645             650             655

Gly Cys Thr Thr Ala Ala Cys Thr Thr Gly Ala Cys Thr Cys Cys Gly
            660             665             670

Gly Cys Gly Thr Ala Thr Cys Cys Ala Gly Cys Ala Ala Gly Thr Gly
            675             680             685

Ala Gly Ala Ala Ala Gly Ala Ala Gly Ala Ala Thr Ala Ala
690                 695             700

Ala Cys Thr Gly Gly Cys Thr Gly Cys Ala Cys Ala Gly Thr Ala Thr
705                 710             715             720

Gly Cys Ala Gly Ala Thr Gly Gly Cys Thr Thr Thr Gly Cys Cys Ala
            725             730             735

Ala Thr Cys Gly Cys Thr Gly Gly Thr Thr Cys Cys Thr Thr Gly Ala
            740             745             750

Cys Cys Cys Gly Ala Thr Cys Thr Thr Cys Ala Ala Gly Gly Gly Thr
            755             760             765

Ala Ala Cys Thr Ala Thr Cys Cys Gly Gly Ala Gly Gly Ala Cys Ala
            770             775             780

Thr Gly Ala Thr Gly Gly Ala Ala Thr Gly Thr Ala Cys Ala Gly
785                 790             795             800

Cys Ala Ala Ala Ala Thr Thr Ala Thr Thr Gly Gly Gly Gly Ala Ala
            805             810             815

Thr Thr Cys Gly Ala Thr Thr Cys Ala Thr Thr Ala Ala Gly Gly
            820             825             830

Ala Ala Gly Gly Cys Gly Ala Thr Cys Thr Gly Gly Ala Gly Ala Cys

-continued

```
        835                 840                 845

Thr Ala Thr Cys Ala Gly Cys Gly Thr Cys Cys Cys Gly Ala Thr Thr
    850                 855                 860

Gly Ala Cys Thr Thr Cys Thr Thr Ala Gly Gly Cys Ala Thr Cys Ala
865                 870                 875                 880
Ala Thr Thr Ala Cys Thr Ala Cys Ala Cys Thr Cys Gly Gly Ala Gly
                885                 890                 895

Cys Ala Thr Thr Gly Thr Thr Ala Ala Ala Thr Ala Cys Gly Ala Thr
            900                 905                 910

Gly Ala Ala Gly Ala Thr Thr Cys Cys Ala Thr Gly Cys Thr Gly Ala
        915                 920                 925

Ala Ala Gly Cys Ala Gly Ala Gly Ala Ala Cys Gly Thr Ala Cys Cys
    930                 935                 940

Gly Gly Gly Ala Cys Cys Gly Gly Gly Thr Ala Ala Ala Cys Gly Thr
945                 950                 955                 960

Ala Cys Cys Gly Ala Ala Ala Thr Gly Gly Gly Gly Thr Gly Gly Gly
                965                 970                 975

Ala Ala Ala Thr Cys Thr Cys Gly Cys Cys Cys Gly Ala Gly Thr Cys
            980                 985                 990

Ala Cys Thr Gly Thr Ala Cys Gly  Ala Cys Thr Thr Ala  Cys Thr Gly
        995                 1000                1005

Ala Ala  Ala Cys Gly Cys Thr  Thr Ala Gly Ala Cys  Cys Gly Thr
    1010                1015                1020

Gly Ala  Gly Thr Ala Thr Ala  Cys Gly Ala Ala Ala  Cys Thr Gly
    1025                1030                1035

Cys Cys  Gly Ala Thr Gly Thr  Ala Thr Ala Thr Cys  Ala Cys Cys
    1040                1045                1050

Gly Ala  Ala Ala Ala Thr Gly  Gly Ala Gly Cys Thr  Gly Cys Gly
    1055                1060                1065

Thr Thr  Thr Ala Ala Ala Gly  Ala Thr Gly Ala Ala  Gly Thr Ala
    1070                1075                1080

Ala Cys  Gly Gly Ala Ala Gly  Ala Thr Gly Gly Thr  Cys Gly Thr
    1085                1090                1095

Gly Thr  Thr Cys Ala Cys Gly  Ala Cys Gly Ala Thr  Gly Ala Ala
    1100                1105                1110

Cys Gly  Cys Ala Thr Cys Gly  Ala Ala Thr Ala Cys  Ala Thr Cys
    1115                1120                1125

Ala Ala  Ala Gly Ala Gly Cys  Ala Cys Cys Thr Gly  Ala Ala Ala
    1130                1135                1140

Gly Cys  Thr Gly Cys Cys Gly  Cys Thr Ala Ala Ala  Thr Thr Thr
    1145                1150                1155

Ala Thr  Cys Gly Gly Gly Gly  Ala Ala Gly Gly Cys  Gly Gly Thr
    1160                1165                1170

Ala Ala  Thr Cys Thr Gly Ala  Ala Ala Gly Gly Ala  Thr Ala Cys
    1175                1180                1185

Thr Thr  Thr Gly Thr Gly Thr  Gly Gly Thr Cys Ala  Thr Thr Ala
    1190                1195                1200

Ala Thr  Gly Gly Ala Cys Ala  Ala Cys Thr Thr Cys  Gly Ala Ala
    1205                1210                1215

Thr Gly  Gly Gly Cys Gly Cys  Ala Thr Gly Gly Cys  Thr Ala Cys
    1220                1225                1230

Thr Cys  Cys Ala Ala Ala Cys  Gly Thr Thr Thr Cys  Gly Gly Cys
    1235                1240                1245
```

| Ala | Thr | Thr | Gly | Thr | Gly | Thr | Ala | Thr | Gly | Thr | Gly | Gly | Ala | Cys |
| | 1250 | | | | 1255 | | | | 1260 | | | | | |

| Thr | Ala | Thr | Ala | Cys | Gly | Ala | Cys | Cys | Cys | Ala | Gly | Ala | Ala | Ala |
| | 1265 | | | | 1270 | | | | 1275 | | | | | |

| Cys | Gly | Cys | Ala | Thr | Thr | Cys | Thr | Gly | Ala | Ala | Gly | Gly | Ala | Thr |
| | 1280 | | | | 1285 | | | | 1290 | | | | | |

| Ala | Gly | Cys | Gly | Cys | Thr | Thr | Gly | Thr | Gly | Gly | Thr | Ala | Cys |
| | 1295 | | | | 1300 | | | | 1305 | | | | |

| Ala | Ala | Ala | Gly | Ala | Gly | Gly | Thr | Gly | Ala | Thr | Thr | Cys | Thr | Gly |
| | 1310 | | | | 1315 | | | | 1320 | | | | | |

| Gly | Ala | Thr | Gly | Ala | Thr | Gly | Gly | Gly | Ala | Thr | Thr | Gly | Ala | Ala |
| | 1325 | | | | 1330 | | | | 1335 | | | | | |

| Gly | Ala | Thr |
| | 1340 | |

<210> SEQ ID NO 42
<211> LENGTH: 1341
<212> TYPE: DNA
<213> ORGANISM: Artificial Sequence
<220> FEATURE:
<223> OTHER INFORMATION: Synthetic Polynucleotide

<400> SEQUENCE: 42

```
atggccaagt tcctcgcga ctttgtatgg ggtacagcca catcgagtta tcagattgaa      60
ggcgcggtga atgaagatgg tcgtacaccg tctatctggg acaccttttc gaaaaccgag     120
ggcaaaacct ataaggcca tacgggtgat gttgcctgtg atcactatca ccgctataag      180
gaagatgtgg aaattctgaa agaaattgga gtcaaagcct accggtttag cattgcatgg     240
ccacgtatct ttcctgagga aggcaaatac aacccgaaag gtatggattt ctacaagaaa     300
ctcattgacg aactgcaaaa gcgcgatatt gttcccgcag cgaccattta tcactgggat     360
ctgccacaat gggcctatga caaaggcggt ggctggctga accgtgagtc catcaaatgg     420
tatgtggagt acgcgaccaa attgtttgaa gaactgggtg atgcgatccc gctgtggatt     480
acccataatg agccatggtg ctcttctatc ctcagttatg gtatcggcga acatgcacct     540
ggtcataaga actatcgcga agcgcttatt gctgcgcatc acatcctgct ctcacatggc     600
gaagcggtca aagcgtttcg cgaaatgaac attaagggga gcaaaatcgg cattacgctt     660
aacttgactc cggcgtatcc agcaagtgag aaagaagaag ataaactggc tgcacagtat     720
gcagatggct ttgccaatcg ctggttcctt gacccgatct tcaagggtaa ctatccggag     780
gacatgatgg aattgtacag caaaattatt ggggaattcg atttcattaa ggaaggcgat     840
ctggagacta tcagcgtccc gattgacttc ttaggcgtca attactacac tcggagcatt     900
gttaaatacg atgaagattc catgctgaaa gcagagaacg taccgggacc gggtaaacgt     960
accgaaatgg ggtgggaaat ctcgcccgag tcactgtacg acttactgaa acgcttagac    1020
cgtgagtata cgaaactgcc gatgtatatc accgaaaatg gagctgcgtt taaagatgaa    1080
gtaacggaag atggtcgtgt tcacgacgat gaacgcatcg aatacatcaa agagcacctg    1140
aaagctgccg ctaaatttat cggggaaggc ggtaatctga aggatacttt tgtgtggtca    1200
ttaatggaca acttcgaatg ggcgcatggc tactccaaac gtttcggcat tgtgtatgtg    1260
gactatgaga cccagaaacg cattctgaag gatagcgcct gtggtacaa agaggtgatt    1320
ctggatgatg ggattgaaga t                                              1341
```

<210> SEQ ID NO 43
<211> LENGTH: 1341
<212> TYPE: DNA
<213> ORGANISM: Artificial Sequence
<220> FEATURE:
<223> OTHER INFORMATION: Synthetic Polynucleotide

<400> SEQUENCE: 43

```
atggccaagt tcctcgcga ctttgtatgg ggtacagcca catcgagtta tcagattgaa      60
ggcgcggtga atgaagatgg tcgtacaccg tctatctggg acaccttttc gaaaaccgag     120
ggcaaaacct ataaggcca tacgggtgat gttgcctgtg atcactatca ccgctataag      180
gaagatgtgg aaattctgaa agaaattgga gtcaaagcct accggtttag cattgcatgg     240
ccacgtatct ttcctgagga aggcaaatac aacccgaaag gtatggattt ctacaagaaa     300
ctcattgacg aactgcaaaa gcgcgatatt gttcccgcag cgaccattta tcactgggat     360
ctgccacaat gggcctatga caaaggcggt ggctggctga accgtgagtc catcaaatgg     420
tatgtggagt acgcgaccaa attgtttgaa gaactgggtg atgcgatccc gctgtggatt     480
acccataatg agccatggtg ctcttctatc ctcagttatg gtatcggcga acatgcacct     540
ggtcataaga actatcgcga agcgcttatt gctgcgcatc acatcctgct ctcacatggc     600
gaagcggtca aagcgtttcg cgaaatgaac attaagggga gcaaaatcgg cattacgctt     660
aacttgactc cggcgtatcc agcaagtgag aagaagaag ataaactggc tgcacagtat      720
gcagatggct ttgccaatcg ctggttcctt gacccgatct tcaagggtaa ctatccggag     780
gacatgatgg aattgtacag caaaattatt ggggaattcg atttcattaa ggaaggcgat     840
ctggagacta tcagcgtccc gattgacttc ttaggcgtca attactacac tcggagcatt     900
gttaaatacg atgaagattc catgctgaaa gcagagaacg taccgggacc gggtaaacgt     960
accgaaatgg ggtgggaaat ctcgcccgag tcactgtacg acttactgaa acgcttagac    1020
cgtgagtata cgaaactgcc gatgtatatc accgaaaatg gagctgcgtt taaagatgaa    1080
gtaacggaag atggtcgtgt tcacgacgat gaacgcatcg aatacatcaa agagcacctg    1140
aaagctgccg ctaaatttat cggggaaggc ggtaatctga aggatactt tgtgtggtca     1200
ttaatggaca acttcgaatg ggcgcatggc tactccaaac gtttcggcat tgtgtatgtg    1260
gactatacga cccagaaacg cattctgaag gatagcgcct tgtggtacaa agaggtgatt    1320
cgtgatgatg ggattgaaga t                                              1341
```

<210> SEQ ID NO 44
<211> LENGTH: 447
<212> TYPE: PRT
<213> ORGANISM: Thermoanaerobacter brockii

<400> SEQUENCE: 44

```
Met Ala Lys Phe Pro Arg Asp Phe Val Trp Gly Thr Ala Thr Ser Ser
1               5                   10                  15

Tyr Gln Ile Glu Gly Ala Val Asn Glu Asp Gly Arg Thr Pro Ser Ile
            20                  25                  30

Trp Asp Thr Phe Ser Lys Thr Glu Gly Lys Thr Tyr Lys Gly His Thr
        35                  40                  45

Gly Asp Val Ala Cys Asp His Tyr His Arg Tyr Lys Glu Asp Val Glu
    50                  55                  60

Ile Leu Lys Glu Ile Gly Val Lys Ala Tyr Arg Phe Ser Ile Ala Trp
65                  70                  75                  80

Pro Arg Ile Phe Pro Glu Glu Gly Lys Tyr Asn Pro Lys Gly Met Asp
```

```
                    85                  90                  95
Phe Tyr Lys Lys Leu Ile Asp Glu Leu Gln Lys Arg Asp Ile Val Pro
            100                 105                 110
Ala Ala Thr Ile Tyr His Trp Asp Leu Pro Gln Trp Ala Tyr Asp Lys
            115                 120                 125
Gly Gly Gly Trp Leu Asn Arg Glu Ser Ile Lys Trp Tyr Val Glu Tyr
            130                 135                 140
Ala Thr Lys Leu Phe Glu Glu Leu Gly Asp Ala Ile Pro Leu Trp Ile
145                 150                 155                 160
Thr His Asn Glu Pro Trp Cys Ser Ser Ile Leu Ser Tyr Gly Ile Gly
                    165                 170                 175
Glu His Ala Pro Gly His Lys Asn Tyr Arg Glu Ala Leu Ile Ala Ala
                    180                 185                 190
His His Ile Leu Leu Ser His Gly Glu Ala Val Lys Ala Phe Arg Glu
                    195                 200                 205
Met Asn Ile Lys Gly Ser Lys Ile Gly Ile Thr Leu Asn Leu Thr Pro
            210                 215                 220
Ala Tyr Pro Ala Ser Glu Lys Glu Asp Lys Leu Ala Ala Gln Tyr
225                 230                 235                 240
Ala Asp Gly Phe Ala Asn Arg Trp Phe Leu Asp Pro Ile Phe Lys Gly
                    245                 250                 255
Asn Tyr Pro Glu Asp Met Met Glu Leu Tyr Ser Lys Ile Ile Gly Glu
                    260                 265                 270
Phe Asp Phe Ile Lys Glu Gly Asp Leu Glu Thr Ile Ser Val Pro Ile
                    275                 280                 285
Asp Phe Leu Gly Val Asn Tyr Tyr Thr Arg Ser Ile Val Lys Tyr Asp
            290                 295                 300
Glu Asp Ser Met Leu Lys Ala Glu Asn Val Pro Gly Pro Gly Lys Arg
305                 310                 315                 320
Thr Glu Met Gly Trp Glu Ile Ser Pro Glu Ser Leu Tyr Asp Leu Leu
                    325                 330                 335
Lys Arg Leu Asp Arg Glu Tyr Thr Lys Leu Pro Met Tyr Ile Thr Glu
                    340                 345                 350
Asn Gly Ala Ala Phe Lys Asp Glu Val Thr Glu Asp Gly Arg Val His
                    355                 360                 365
Asp Asp Glu Arg Ile Glu Tyr Ile Lys Glu His Leu Lys Ala Ala Ala
            370                 375                 380
Lys Phe Ile Gly Glu Gly Gly Asn Leu Lys Gly Tyr Phe Val Trp Ser
385                 390                 395                 400
Leu Met Asp Asn Phe Glu Trp Ala His Gly Tyr Ser Lys Arg Phe Gly
                    405                 410                 415
Ile Val Tyr Val Asp Tyr Thr Thr Gln Lys Arg Ile Leu Lys Asp Ser
                    420                 425                 430
Ala Leu Trp Tyr Lys Glu Val Ile Leu Asp Asp Gly Ile Glu Asp
                    435                 440                 445
```

<210> SEQ ID NO 45
<211> LENGTH: 33
<212> TYPE: DNA
<213> ORGANISM: Artificial Sequence
<220> FEATURE:
<223> OTHER INFORMATION: Mutagenesis Primer

<400> SEQUENCE: 45
agcgcgatat taaacccgca gcgaccattt atc                                33

<210> SEQ ID NO 46
<211> LENGTH: 33
<212> TYPE: DNA
<213> ORGANISM: Artificial Sequence
<220> FEATURE:
<223> OTHER INFORMATION: Mutagenesis Primer

<400> SEQUENCE: 46
gataaatggt cgctgcgggt ttaatatcgc gct            33

<210> SEQ ID NO 47
<211> LENGTH: 33
<212> TYPE: DNA
<213> ORGANISM: Artificial Sequence
<220> FEATURE:
<223> OTHER INFORMATION: Mutragenesis Primer

<400> SEQUENCE: 47
cgattgactt cttaggcatc aattactaca ctc            33

<210> SEQ ID NO 48
<211> LENGTH: 33
<212> TYPE: DNA
<213> ORGANISM: Artificial Sequence
<220> FEATURE:
<223> OTHER INFORMATION: Mutagenesis Primer

<400> SEQUENCE: 48
gagtgtagta attgatgcct aagaagtcaa tcg            33

<210> SEQ ID NO 49
<211> LENGTH: 32
<212> TYPE: DNA
<213> ORGANISM: Artificial Sequence
<220> FEATURE:
<223> OTHER INFORMATION: Mutagenesis Primer

<400> SEQUENCE: 49
attgtgtatg tggactatga gacccagaaa cg             32

<210> SEQ ID NO 50
<211> LENGTH: 32
<212> TYPE: DNA
<213> ORGANISM: Artificial Sequence
<220> FEATURE:
<223> OTHER INFORMATION: Mutegenesis Primer

<400> SEQUENCE: 50
cgtttctggg tctcatagtc cacatacaca at             32

<210> SEQ ID NO 51
<211> LENGTH: 33
<212> TYPE: DNA
<213> ORGANISM: Artificial Sequence
<220> FEATURE:
<223> OTHER INFORMATION: Mutagenesis Primer

<400> SEQUENCE: 51
acaaagaggt gattcgcgat gatgggattg aag            33

<210> SEQ ID NO 52
<211> LENGTH: 33
<212> TYPE: DNA
<213> ORGANISM: Artificial Sequence
<220> FEATURE:
<223> OTHER INFORMATION: Mutagenesis Primer

<400> SEQUENCE: 52
cttcaatccc atcatcgcga atcacctctt tgt                33

MUTANT BETA-GLUCOSIDASE VARIANTS WITH INCREASED THERMOSTABILITY

CROSS-REFERENCE TO RELATED APPLICATIONS

This application is a U.S. National Stage of PCT/EP2016/070804, filed on Sep. 5, 2016, which claims priority of German Patent Application No. 10 2015 117 534.7, filed on Oct. 15, 2015, each of which is incorporated herein by reference.

SEQUENCE LISTING INCORPORATION

Biological sequence information for this application is included in an ASCII text file, having the file name "eolfseql.txt" and a having file size of 171 KB, which is part of said PCT/EP2016/070804 and is incorporated herein by reference.

FIELD OF THE INVENTION

The invention relates to mutant variants of the β-glucosidase CglT from *Thermoanaerobacter brockii* and nucleic acids for producing the same. Said mutant variants show significantly increased thermostability and enzyme activity. Furthermore, the invention provides vectors, host cells and methods for producing said mutant variants of the β-glucosidase CglT. Also provided are artificial cellulosomes comprising the mutant variants of the β-glucosidase CglT and methods for the enzymatic hydrolysis of cellulosic biomass comprising said artificial cellulosomes and/or said mutant variants of the β-glucosidase CglT.

BACKGROUND OF THE INVENTION

Biomass contains a variety of polysaccharides as structural or storage compounds. Cellulose and hemicellulose are the most prominent. The amount and ease of availability makes biomass a rich, renewable energy source. About half of the carbonaceous compounds in terrestrial biomass are cellulose, which is the most prominent single organic compound on earth. Almost all of the biomass produced is mineralized again by enzymes provided by microorganisms. Thus, polysaccharide hydrolysis is one of the most important enzymatic processes on earth. Whereas hemicellulose has an extremely heterogeneous chemical composition, cellulose is a chemically homogeneous linear polymer of up to 10,000 D-glucose molecules, which are connected by β-1,4 bonds. Because each glucose residue is tilted by 180° towards its neighbor, the structural subunit of cellulose is cellobiose. The chemical uniformity provokes spontaneous crystallization of the cellulose molecules: hydrogen bonding within and between multiple layers of parallel molecules results in the formation of tightly packed microfibrils. Cellulose is a sturdy material, ideally suited to insure the structural stability of land plants, where it is a main component of the primary cell wall, especially in wood. Although crystalline cellulose is chemically homogeneous, no single enzyme is able to hydrolyze it, whereas soluble cellulose derivatives are easily degraded by a single endo-β-1,4-glucanase. The extensive, level surface of the insoluble crystalline microfibrils is an unusually resilient substrate for hydrolytic enzymes. Enzyme mechanisms generally depend on single molecules fitting in their substrate pocket. This—besides the tight conjunction with other polymers, like hemicellulose and lignin—makes cellulose-containing materials like wood withstanding rotting and weathering. The crystalline material is only hydrolyzed by a cluster of simultaneously present, interacting enzymes, or alternatively by a multienzyme complex. Only by cooperation with non-catalytic, specific binding modules, are the enzymes able to disrupt the crystal surface at the solid-liquid interphase, to make single cellulose fibers accessible for hydrolysis. However, insoluble cellulose is not a homogeneous crystal. Rather, it is a polymorphous, insoluble material, adding to the difficulty of binding to it.

Enzymatic cellulose hydrolysis is generally a slow and incomplete process. Due to the highly ordered, insoluble, crystalline nature of the cellulose, very few microorganisms possess the necessary enzymatic system to efficiently degrade cellulosic substrates to soluble sugar. Highly efficient cellulose degradation has been demonstrated by a multienzyme complex termed cellulosome produced by anaerobic, thermophilic, cellulolytic bacteria, like for example *Clostridium thermocellum* (Schwarz 2001). The cellulosome contains a noncatalytic subunit called scaffoldin that binds the insoluble substrate via a cellulose-specific carbohydrate-binding module (CBM). The *C. thermocellum* scaffoldin also contains a set of nine subunit-binding modules coined cohesins that mediate the specific incorporation and organization of the catalytic subunits through a complementary binding module (dockerin) that is carried by each enzymatic subunit. The scaffoldin contains another type of dockerin (type II) at its C terminus that mediates the attachment of the cellulosome to the cell wall through a selective binding interaction with a set of cell-anchoring proteins. The assembly of the enzymes into the complex ensures their collective targeting to a specific region of the substrate thereby facilitating stronger synergism among the catalytic components. The synergistic degradation of the different enzymes comprising the cellulosome results in the formation of large concentrations of the major soluble disaccharide end product cellobiose. The cellobiose acts as a strong end product inhibitor, mainly for exocellulases; near-complete inhibition of the *C. thermocellum* cellulosome occurs at a concentration of 2% cellobiose. Therefore, in a cell-free system, removal of the inhibitory cellobiose is essential for constant degradation of the lignocellulose substrate (Gefen et al. 2012).

Previous work has shown that addition of the cellobiose degrading enzyme β-glucosidase can enhance the rate and degree of solubilization of crystalline cellulose by the *C. thermocellum* cellulosome (Schwarz 2001, Prawitwong et al. 2013). It does so by converting cellobiose to two molecules of non-inhibitory glucose. The glucose molecules in turn may lead to a feedback-inhibition of the β-glucosidase.

The CglT β-glucosidase from *Thermoanaerobacter brockii* was first described by Breves et al., 1997. The native protein consists of 446 amino acids with a molecular weight of 52 kDa.

WO 2010/099500 discloses variants of the *Thermoanaerobacter brockii* CglT β-glucosidase that have improved β-glucosidase activity compared to the wild type enzyme. Also disclosed therein are polynucleotides that encode the variants, as well as methods of producing the variants, enzyme compositions comprising the variants and methods for using the variants in industrial applications. WO 2010/099500 does not disclose mutations at positions E40, V111, V293, T423 and L441 in the *Thermoanaerobacter brockii* CglT β-glucosidase as claims in the present application.

WO 2010/148148 discloses recombinantly produced β-glucosidase variants with enhanced thermoactivity compared to naturally occurring proteins. Also provided are methods for producing a variant β-glucosidase polypeptide with improved thermoactivity by identifying performance sensitive positions in a target β-glucosidase polypeptide and substituting the residue at a respective position with a thermoactivity enhancing residue. WO 2010/148148 does not disclose variants of the CglT β-glucosidase from *Thermoanaerobacter brockii*.

Artificial cellulosomes and the use of the same for enzymatic break down of resilient substrates is disclosed in EP 2410061 and WO 2012/010295.

SUMMARY OF THE INVENTION

Figure 1:
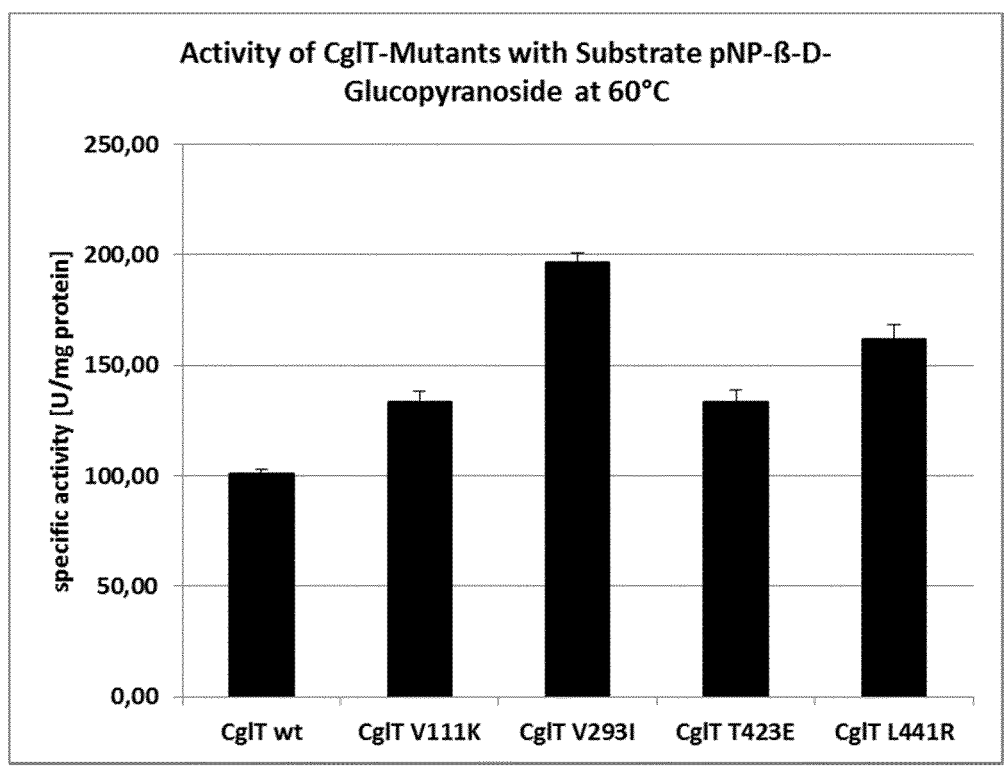
FIG. 1 shows the specific enzyme activities of the wild type (left) enzyme and of the CglT-mutants V111K, V293I, T423E and L441R (from left to right) in [U/mg] using 20 mM substrate p-NPG (p-nitrophenyl-β-D-glycoside). Reaction conditions of the assay: 60° C., 15 ng enzyme, 1×MOPS buffer, reaction time 30 min. Determinations were performed in triplicate.

The mutant polypeptides of the present invention result from the mutagenesis of the wild type polypeptide of SEQ ID NO: 44, which is the β-glucosidase CglT isolated from the thermophilic bacterium *Thermoanaerobacter brockii*. The wild type enzyme is relatively thermostable and the enzyme does not show a remarkable loss of activity after two days of incubation at 60° C. (Breves et al., 1997). However, a process temperature of 60° C. in industrial processes for the degradation of cellulosic biomass is still too low, because the risk for microbial contaminations cannot be effectively excluded and the dissolution of the cellulose microcrystals is not sufficient in order to make the bulk part of the crystalline cellulose available as substrate for cellulases used in the biomass degradation processes.

It was thus an object of the present invention to overcome the disadvantages of the prior art, in particular the disadvantages of the wild type CglT β-glucosidase.

Accordingly, the present invention provides mutant polypeptides, which show an improved thermostability compared to the wild type enzyme. The mutant polypeptides according to the invention do not only show an improved thermostability, but also a significantly increased enzyme activity. The mutant β-glucosidase polypeptides of the present invention can be used in processes for the degradation of cellulosic biomass to effectively degrade cellobiose, which is the resulting product of the degradation of cellulose by cellulases, to glucose monomers, thereby preventing the end product inhibition of the cellulases by cellobiose.

It has been shown that mutations at positions E40, V111, V293, T423 and L441 in the wildtype polypeptide of SEQ ID NO: 44 are particularly effective to increase the thermostability and/or the β-glucosidase enzyme activity of the mutant polypeptides of the invention.

The present invention thus provides a mutant polypeptide comprising, consisting essentially of or consisting of the amino acid sequence of SEQ ID NO: 1 or a polypeptide having an amino acid sequence that is at least 70% identical thereto:

(SEQ ID NO: 1)
MAKFPRDFVWGTATSSYQIEGAVNEDGRTPSIWDTFSKTX$_1$GKTYKGHTG

DVACDHYHRYKEDVEILKEIGVKAYRFSIAWPRIFPEEGKYNPKGMDFYK

KLIDELQKRDIX$_2$PAATIYHWDLPQWAYDKGGGWLNRESIKWYVEYATKL

FEELGDAIPLWITHNEPWCSSILSYGIGEHAPGHKNYREALIAAHHILLS

HGEAVKAFREMNIKGSKIGITLNLTPAYPASEKEEDKLAAQYADGFANRW

FLDPIFKGNYPEDMMELYSKIIGEFDFIKEGDLETISVPIDFLGX$_3$NYYT

RSIVKYDEDSMLKAENVPGPGKRTEMGWEISPESLYDLLKRLDREYTKLP

MYITENGAAFKDEVTEDGRVHDDERIEYIKEHLKAAAKFIGEGGNLKGYF

VWSLMDNFEWAHGYSKRFGIVYVDYX$_4$TQKRILKDSALWYKEVIX$_5$DDGI

ED;

wherein

X$_1$ is selected from E, P, T, M, A, S and G;

X$_2$ is selected from V, K, R and H;

X$_3$ is selected from V, I, L, M, P, T and A;

X$_4$ is selected from T, E, D, N, Q, M and P; and

X$_5$ is selected from L, R, K and H;

with the proviso that the mutant polypeptide of SEQ ID NO: 1 does not comprise, consist essentially of or consist of the amino acid sequence of the wild type polypeptide of SEQ ID NO: 44.

DETAILED DESCRIPTION OF THE INVENTION

The present invention provides a mutant polypeptide comprising, consisting essentially of or consisting of the amino acid sequence of SEQ ID NO. 1 or a polypeptide having an amino acid sequence that is at least 70% identical thereto:

(SEQ ID NO: 1)
MAKFPRDFVWGTATSSYQIEGAVNEDGRTPSIWDTFSKTX$_1$GKTYKGHT

GDVACDHYHRYKEDVEILKEIGVKAYRFSIAWPRIFPEEGKYNPKGMDF

YKKLIDELQKRDIX$_2$PAATIYHWDLPQWAYDKGGGWLNRESIKWYVEYA

TKLFEELGDAIPLWITHNEPWCSSILSYGIGEHAPGHKNYREALIAAHH

ILLSHGEAVKAFREMNIKGSKIGITLNLTPAYPASEKEEDKLAAQYADG

FANRWFLDPIFKGNYPEDMMELYSKIIGEFDFIKEGDLETISVPIDFLG

X$_3$NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYX$_4$TQKRILKDSALWYK

EVIX$_5$DDGIED;

wherein
X$_1$ is selected from E, P, T, M, A, S and G;
X$_2$ is selected from V, K, R and H;
X$_3$ is selected from V, I, L, M, P, T and A;
X$_4$ is selected from T, E, D, N, Q, M and P; and
X$_5$ is selected from L, R, K and H;
with the proviso that the mutant polypeptide of SEQ ID NO: 1 does not comprise, consist essentially of or consist of the amino acid sequence of the wild type polypeptide of SEQ ID NO: 44.

The terms "polypeptide", "peptide", and "protein", as used herein, are interchangeable and are defined to mean a biomolecule composed of amino acids linked by a peptide bond.

If peptide or amino acid sequences are mentioned herein, each amino acid residue is represented by a one-letter or a three-letter designation, corresponding to the trivial name of the amino acid, in accordance with the following conventional list:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The terms "a", "an" and "the" as used herein are defined to mean "one or more" and include the plural unless the context is inappropriate.

In a preferred embodiment, the invention provides a mutant polypeptide, comprising, consisting essentially of or consisting of the amino acid sequence of SEQ ID NO. 2 or a polypeptide having an amino acid sequence that is at least 70% identical thereto:

(SEQ ID NO: 2)
MAKFPRDFVWGTATSSYQIEGAVNEDGRTPSIWDTFSKTPGKTYKGHTG

DVACDHYHRYKEDVEILKEIGVKAYRFSIAWPRIFPEEGKYNPKGMDFY

KKLIDELQKRDIX$_2$PAATIYHWDLPQWAYDKGGGWLNRESIKWYVEYAT

KLFEELGDAIPLWITHNEPWCSSILSYGIGEHAPGHKNYREALIAAHHI

LLSHGEAVKAFREMNIKGSKIGITLNLTPAYPASEKEEDKLAAQYADGF

ANRWFLDPIFKGNYPEDMMELYSKIIGEFDFIKEGDLETISVPIDFLG

X$_3$NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYX$_4$TQKRILKDSALWYK

EVIX$_5$DDGIED, wherein the mutant polypeptide of SEQ ID NO: 2 comprises at least the mutation E40P; and
X$_2$ is selected from V, K, R and H;
X$_3$ is selected from V, I, L, M, P, T and A;
X$_4$ is selected from T, E, D, N, Q, M and P; and
X$_5$ is selected from L, R, K and H.

In a further preferred embodiment, the invention provides a mutant polypeptide, comprising, consisting essentially of or consisting of the amino acid sequence of SEQ ID NO. 3 or a polypeptide having an amino acid sequence that is at least 70% identical thereto:

(SEQ ID. NO: 3)
MAKFPRDFVWGTATSSYQIEGAVNEDGRTPSIWDTFSKTX$_1$GKTYKGHT

GDVACDHYHRYKEDVEILKEIGVKAYRFSIAWPRIFPEEGKYNPKGMDF

YKKLIDELQKRDIKPAATIYHWDLPQWAYDKGGGWLNRESIKWYVEYAT

KLFEELGDAIPLWITHNEPWCSSILSYGIGEHAPGHKNYREALIAAHHI

LLSHGEAVKAFREMNIKGSKIGITLNLTPAYPASEKEEDKLAAQYADGF

ANRWFLDPIFKGNYPEDMMELYSKIIGEFDFIKEGDLETISVPIDFLG

X$_3$NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYX$_4$TQKRILKDSALWYK

EVIX$_5$DDGIED, wherein the mutant polypeptide of SEQ ID NO: 3 comprises at least the mutation V111K; and
    $X_1$ is selected from E, P, T, M, A, S and G;
    $X_3$ is selected from V, I, L, M, P, T and A;
    $X_4$ is selected from T, E, D, N, Q, M and P; and
    $X_5$ is selected from L, R, K and H.

In a further preferred embodiment, the invention provides a mutant polypeptide comprising, consisting essentially of or consisting of the amino acid sequence of SEQ ID NO. 4 or a polypeptide having an amino acid sequence that is at least 70% identical thereto:

```
                                           (SEQ ID NO: 4)
MAKFPRDFVWGTATSSYQIEGAVNEDGRTPSIWDTFSKTX1GKTYKGHT

GDVACDHYRYKEDVEILKEIGVKAYRFSIAWPRIFPEEGKYNPKGMDF

YKKLIDELQKRDIX2PAATIYHWDLPQWAYDKGGGWLNRESIKWYVEYA

TKLFEELGDAIPLWITHNEPWCSSILSYGIGEHAPGHKNYREALIAAHH

ILLSHGEAVKAFREMNIKGSKIGITLNLTPAYPASEKEEDKLAAQYADG

FANRWFLDPIFKGNYPEDMMELYSKIIGEFDFIKEGDLETISVPIDFLG

INYYTRSIVKYDEDSMLKAENVPGPGKRTEMGWEISPESLYDLLKRLDR

EYTKLPMYITENGAAFKDEVTEDGRVHDDERIEYIKEHLKAAAKFIGEG

GNLKGYFVWSLMDNFEWAHGYSKRFGIVYVDYX4TQKRILKDSALWYKE

VIX5DDGIED,
``` wherein said mutant polypeptide of SEQ ID NO: 4 comprises at least the mutation V293I; and
    $X_1$ is selected from E, P, T, M, A, S and G;
    $X_2$ is selected from V, K, R and H;
    $X_4$ is selected from T, E, D, N, Q, M and P; and
    $X_5$ is selected from L, R, K and H.

In a further preferred embodiment, the invention provides a mutant polypeptide comprising, consisting essentially of or consisting of the amino acid sequence of SEQ ID NO. 5 or a polypeptide having an amino acid sequence that is at least 70% identical thereto:

```
(SEQ ID NO: 5)
MAKFPRDFVWGTATSSYQIEGAVNEDGRTPSIWDTFSKTX1GKTYKGHT

GDVACDHYRYKEDVEILKEIGVKAYRFSIAWPRIFPEEGKYNPKGMDF

YKKLIDELQKRDIX2PAATIYHWDLPQWAYDKGGGWLNRESIKWYVEYA

TKLFEELGDAIPLWITHNEPWCSSILSYGIGEHAPGHKNYREALIAAHH

ILLSHGEAVKAFREMNIKGSKIGITLNLTPAYPASEKEEDKLAAQYADG

FANRWFLDPIFKGNYPEDMMELYSKIIGEFDFIKEGDLETISVPIDFLG

X3NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYETQKRILKDSALWYKE

VIX5DDGIED,
``` wherein said mutant polypeptide of SEQ ID NO: 5 comprises at least the mutation T423E; and
    $X_1$ is selected from E, P, T, M, A, S and G;
    $X_2$ is selected from V, K, R and H;
    $X_3$ is selected from V, I, L, M, P, T and A;
    $X_5$ is selected from L, R, K and H.

In a further preferred embodiment, the invention provides a mutant polypeptide, comprising, consisting essentially of or consisting of the amino acid sequence of SEQ ID NO. 6 or a polypeptide having an amino acid sequence that is at least 70% identical thereto:

```
                                           (SEQ ID NO: 6)
MAKFPRDFVWGTATSSYQIEGAVNEDGRTPSIWDTFSKTX1GKTYKGHT

GDVACDHYRYKEDVEILKEIGVKAYRFSIAWPRIFPEEGKYNPKGMDF

YKKLIDELQKRDIX2PAATIYHWDLPQWAYDKGGGWLNRESIKWYVEYA

TKLFEELGDAIPLWITHNEPWCSSILSYGIGEHAPGHKNYREALIAAHH

ILLSHGEAVKAFREMNIKGSKIGITLNLTPAYPASEKEEDKLAAQYADG

FANRWFLDPIFKGNYPEDMMELYSKIIGEFDFIKEGDLETISVPIDFLG

X3NYYTRSIVKYDEDSMLKAENVPGPGKRTEMGWEISPESLYDLLKRLD

REYTKLPMYITENGAAFKDEVTEDGRVHDDERIEYIKEHLKAAAKFIGE

GGNLKGYFVWSLMDNFEWAHGYSKRFGIVYVDYX4TQKRILKDSALWYK

EVIRDDGIED,
``` wherein said mutant polypeptide of SEQ ID NO: 6 comprises at least the mutation L441R; and
    $X_1$ is selected from E, P, T, M, A, S and G;
    $X_2$ is selected from V, K, R and H;
    $X_3$ is selected from V, I, L, M, P, T and A;
    $X_4$ is selected from T, E, D, N, Q, M and P; and
    In regard to the mutant polypeptides of SEQ ID NOs: 1 to 6:
    $X_1$ is preferably selected from E, P, T, M, A and S, or from E, P, T, M and A; or from E, P, T and M.
    More preferably, $X_1$ is selected from E, P and T or from E and P
    Most preferably, $X_1$ is P.
    $X_2$ is preferably selected from V, K and R.
    More preferably, $X_2$ is V or K.
    Most preferably, $X_2$ is K.
    $X_3$ is preferably selected from V, I, L, M, P and T, or from V, I, L, M and P or from V, I, L and M.
    More preferably, $X_3$ is selected from V, I and L or from V and I.
    Most preferably, $X_3$ is I.
    $X_4$ is preferably selected from T, E, D, N, Q and M, or from T, E, D, N, and Q, or from T, E, D, and N.
    More preferably, $X_4$ is selected from T, E, and D, or from T and E.
    Most preferably, $X_4$ is E.
    $X_5$ is preferably selected from L, R and K.
    More preferably, $X_5$ is L or R.
    Most preferably, $X_5$ is R.

Preferably, at at least one position of $X_1$, $X_2$, $X_3$, $X_4$ and $X_5$ in the mutant polypeptides of any one of SEQ ID NOS: 1 to 6, the amino acid of the wild type sequence (SEQ ID NO: 44) is exchanged by substitution, i.e. in a preferred embodiment, the mutant polypeptide according to the invention does not comprise, consist essentially of or consist of the amino acid sequence of the wild type polypeptide of SEQ ID NO: 44.

In a most preferred embodiment, the mutant polypeptides of any one of SEQ ID NOS: 1 to 6 or polypeptides having an amino acid sequence that is at least 70% identical thereto do not comprise, consist essentially of or consist of the amino acid sequence of the wild type polypeptide of SEQ ID NO: 44.

Further most preferably, the invention provides a mutant polypeptide comprising a single mutation selected from E40P, V111K, V293I, T423E and L441R, wherein said mutant polypeptide comprises, essentially consists of or consists of the amino acid sequence selected from the group consisting of SEQ ID NOs: 7, 8, 9, 10 and 11:

| | |
|---|---|
| E40P, | SEQ ID NO: 7; |
| V111K, | SEQ ID NO: 8; |
| V293I, | SEQ ID NO: 9; |
| T423E, | SEQ ID NO: 10; and |
| L441R, | SEQ ID NO: 11. |

Thermostability and/or β-glucosidase activity of the mutant polypeptides of the invention is further improved and/or increased by introducing at least two mutations into the wild type sequence of SEQ ID NO: 44. Accordingly, in a further preferred embodiment, the invention provides a mutant polypeptide, which comprises a combination of two mutations and which comprises, essentially consists of or consists of an amino acid sequence selected from the group consisting of SEQ ID NOs: 12-21:

| | |
|---|---|
| E40P; V111K; | SEQ ID NO: 12; |
| E40P; V293I; | SEQ ID NO: 13; |
| E40P; T423E; | SEQ ID NO: 14; |
| E40P; L441R; | SEQ ID NO: 15; |
| V111K; V293I; | SEQ ID NO: 16; |
| V111K; T423E; | SEQ ID NO: 17; |
| V111K; L441R; | SEQ ID NO: 18; |
| V293I; T423E; | SEQ ID NO: 19; |
| V293I; L441R; | SEQ ID NO: 20; and |
| T423E; L441R; | SEQ ID NO: 21. |

Thermostability and/or β-glucosidase activity of the mutant polypeptides of the invention is further improved and/or increased by introducing at least three mutations into the wild type sequence of SEQ ID NO: 44. Accordingly, in a further preferred embodiment, the invention provides a mutant polypeptide, which comprises a combination of three mutations and which comprises, essentially consists of or consists of an amino acid sequence selected from the group consisting of SEQ ID NOs: 22-31:

| | |
|---|---|
| E40P; V111K; V293I; | SEQ ID NO: 22; |
| E40P; V111K; T423E; | SEQ ID NO: 23; |
| E40P; V111K; L441R; | SEQ ID NO: 24; |
| E40P; V293I; T423E; | SEQ ID NO: 25; |
| E40P; V293I; L441R; | SEQ ID NO: 26; |
| E40P; T423E; L441R; | SEQ ID NO: 27; |
| V111K; V293I; T423E; | SEQ ID NO: 28; |
| V111K; V293I; L441R; | SEQ ID NO: 29; |
| V111K; T423E; L441R; | SEQ ID NO: 30; and |
| V293I; T423E; L441R | SEQ ID NO: 31. |

Thermostability and/or β-glucosidase activity of the mutant polypeptides of the invention is further improved and/or increased by introducing at least four mutations into the wild type sequence of SEQ ID NO: 44. Accordingly, in a further preferred embodiment, the invention provides a mutant polypeptide, which comprises a combination of four mutations and the mutant polypeptide comprises, essentially consists of or consists of an amino acid sequence selected from the group consisting of SEQ ID NOs: 32-36:

| | |
|---|---|
| E40P; V111K; V293I; T423E; | SEQ ID NO: 32; |
| E40P; V111K; V293I; L441R; | SEQ ID NO: 33; |
| E40P; V111K; T423E; L441R; | SEQ ID NO: 34; |
| E40P; V293I; T423E; L441R; | SEQ ID NO: 35; and |
| V111K; V293I; T423E; L441R; | SEQ ID NO: 36. |

Thermostability and/or β-glucosidase activity of the mutant polypeptides of the invention is further improved and/or increased by introducing five mutations into the wild type sequence of SEQ ID NO: 44. Accordingly, in a further preferred embodiment, the invention provides a mutant polypeptide, which comprises a combination of the five mutations, wherein the mutant polypeptide comprises, essentially consists of or consists of the amino acid sequence of SEQ ID NO: 37:

E40P; V111K; V293I; T423E; L441R; SEQ ID NO: 37.

In a preferred embodiment, the thermostability of the mutant polypeptides of the invention is increased by up to 10%, more preferably up to 15%, up to 20%, up to 25% or up to 30%, most preferably up to 35%, up to 40% or more. "Increased thermostability" means that the mutant polypeptides of the invention show a higher specific β-glucosidase enzyme activity at 65° C. or higher for a duration of at least 24 hours, preferably for at least 48 hours, more preferably for at least 72 hours, compared to the wild type enzyme.

In a further preferred embodiment, the specific β-glucosidase enzyme activity of the mutant polypeptides of the invention is increased by up to 20%, up to 30% or up to 40%, more preferably up to 50%, up to 60% or up to 70%, most preferably up to 80%, up to 90%, up to 100% or more. Specific activity is defined as $\mu mol \cdot min^{-1} \cdot mg^{-1}$ (μmol product formation per minute and per mg of active enzyme).

The invention further provides a method for producing mutant polypeptides having mutations in the amino acid residues of the wild type enzyme of SEQ ID NO: 44. Preferably, these mutations improve the thermostability and/or the β-glucosidase enzyme activity of the mutant polypeptides of the invention. The method for producing the mutant polypeptides includes the steps of:
  (a) modifying nucleic acids encoding the amino acid residues that are responsible for thermostability and/or β-glucosidase enzyme activity in the polypeptides from the wild type nucleic acid,
  (b) culturing host cells so that these nucleic acids are expressed; and
  (c) recovering the polypeptides from the host cell culture.

The phrase "modify nucleic acids" in the above-mentioned methods of the present invention refers to modifying nucleic acids so that they correspond to amino acid residues introduced by the "mutations" of the present invention. More specifically, it refers to modifying the nucleic acids encoding the original (wild type) amino acid residues to the nucleic acids encoding the amino acid residues that are to be introduced by the mutation. Ordinarily, it means performing gene manipulations or mutation treatment that would result in at least one nucleotide insertion, deletion, or substitution of the original nucleic acid so that codons encoding amino acid residues of interest are formed. More specifically, codons encoding the original (wild type) amino acid residues are substituted with codons encoding the amino acid residues that are to be introduced by the modification. Such nucleic acid modification can be performed suitably by those skilled in the art using known techniques such as site-specific mutagenesis (see for example, Kunkel (1985) Proc. Natl. Acad. Sci. USA 82: 488), PCR mutagenesis, and cassette mutagenesis.

The invention further provides a nucleic acid, which encodes a mutant polypeptide selected from SEQ ID NOs: 1 to 37.

The "polynucleotides" or "nucleic acids" of the present invention may be in the form of RNA or in the form of DNA; DNA should be understood to include cDNA, genomic DNA, recombinant DNA and synthetic DNA. The DNA may be double-stranded or single-stranded and, if single stranded, may be the coding strand or non-coding (antisense) strand. The coding sequence, which encodes the polypeptide may be identical to the coding sequence shown in SEQ ID NOs 1 to 37, or it may be a different coding sequence encoding the same polypeptide, as a result of the redundancy or degeneracy of the genetic code or a single nucleotide polymorphism. For example, it may also be an RNA transcript which includes the entire length of any one of SEQ ID NOs 1 to 37.

The nucleic acids which encode the polypeptides of SEQ ID NOs: 1 to 37 may include but are not limited to the coding sequence for the polypeptide alone; the coding sequence for the polypeptide plus additional coding sequence, such as a leader or secretory sequence or a proprotein sequence; and the coding sequence for the polypeptide (and optionally additional coding sequence) plus non-coding sequence, such as introns or a non-coding sequence 5' and/or 3' of the coding sequence for the polypeptide.

Thus, the term "polynucleotide encoding a polypeptide" or the term "nucleic acid encoding a polypeptide" should be understood to encompass a polynucleotide or nucleic acid which includes only coding sequence for mutant β-glucosidase, e.g. polypeptide selected from SEQ ID NOs: 1 to 37 as well as one which includes additional coding and/or non-coding sequence. The terms polynucleotides and nucleic acid are used interchangeably.

The present invention also includes polynucleotides where the coding sequence for the polypeptide may be fused in the same reading frame to a polynucleotide sequence which aids in expression and secretion of a polypeptide from a host cell; for example, a leader sequence which functions as a secretory sequence for controlling transport of a polypeptide from the cell may be so fused. The polypeptide having such a leader sequence is termed a preprotein or a preproprotein and may have the leader sequence cleaved, by the host cell to form the mature form of the protein. These polynucleotides may have a 5' extended region so that it encodes a proprotein, which is the mature protein plus additional amino acid residues at the N-terminus. The expression product having such a prosequence is termed a proprotein, which is an inactive form of the mature protein; however, once the prosequence is cleaved an active mature protein remains. The additional sequence may also be attached to the protein and be part of the mature protein. Thus, for example, the polynucleotides of the present invention may encode polypeptides, or proteins having a prosequence, or proteins having both a prosequence and a presequence (leader sequence).

The polynucleotides of the present invention may also have the coding sequence fused in frame to a marker sequence which allows for purification of the polypeptides of the present invention. The marker sequence may be an affinity tag or an epitope tag such as a polyhistidine tag, a streptavidin tag, a Xpress tag, a FLAG tag, a cellulose or chitin binding tag, a glutathione-S transferase tag (GST), a hemagglutinin (HA) tag, a c-myc tag or a V5 tag.

The HA tag would correspond to an epitope derived from the influenza hemagglutinin protein (Wilson, I., etal., Cell, 37: 767 (1984)), and the c-myc tag may be an epitope from human Myc protein (Evans, G. I. et al., Mol. Cell. Biol. 5: 3610-3616(1985)).

The present invention is considered to further provide polynucleotides which hybridize to the hereinabove-described sequences wherein there is at least 70%, preferably at least 90%, and more preferably at least 95% identity or similarity between the sequences, and thus encode proteins having similar biological activity. Moreover, as known in the art, there is "similarity" between two polypeptides when the amino acid sequences contain the same or conserved amino acid substitutes for each individual residue in the sequence. Identity and similarity may be measured using sequence analysis software (e. g., ClustalW at PBIL (Pôle Bioinformatique Lyonnais) http://npsa-pbil.ibcp.fr). The present invention particularly provides such polynucleotides, which hybridize under stringent conditions to the hereinabove-described polynucleotides. As herein used, the term "stringent conditions" means conditions which permit hybridization between polynucleotides sequences and the polynucleotide sequences of SEQ ID NOS: 38 to 43 where there is at least about 70% identity.

Suitably stringent conditions can be defined by, e. g., the concentrations of salt or formamide in the prehybridization and hybridization solutions, or by the hybridization temperature, and are well known in the art. In particular, stringency can be increased by reducing the concentration of salt, by increasing the concentration of formamide, and/or by raising the hybridization temperature.

For example, hybridization under high stringency conditions may employ about 50% formamide at about 37° C. to 42° C., whereas hybridization under reduced stringency conditions might employ about 35% to 25% formamide at about 30° C. to 35° C. One particular set of conditions for hybridization under high stringency conditions employs 42° C., 50% formamide, 5×SSPE, 0.3% SDS, and 200 μg/ml sheared and denatured salmon sperm DNA. For hybridization under reduced stringency, similar conditions as described above may be used in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. Preferably, hybridization should occur only if there is at least 95%, and more preferably at least 97%, identity between the sequences. The polynucleotides which hybridize to the hereinabove described polynucleotides in a preferred embodiment encode polypeptides which exhibit substantially the same biological function or activity as the mature protein encoded by one of the cDNAs of SEQ ID NOs: 38 to 43.

As mentioned, a suitable polynucleotide probe may have at least 14 bases, preferably 30 bases, and more preferably at least 50 bases, and will hybridize to a polynucleotide of the present invention, which has an identity thereto, as hereinabove described, and which may or may not retain activity. For example, such polynucleotides may be employed as a probe for hybridizing to the polynucleotides of SEQ ID NOS: 38 to 43 respectively, for example, for recovery of such a polynucleotide, or as a diagnostic probe, or as a PCR primer. Thus, the present invention includes polynucleotides having at least a 70% identity, preferably at least a 90% identity, and more preferably at least a 95% identity to a polynucleotide which encodes a polypeptide of SEQ ID NOS 1 to 37, as well as fragments thereof, which fragments preferably have at least 30 bases and more preferably at least 50 bases, and to polypeptides encoded by such polynucleotides.

The terms "homology" or "identity," as used interchangeably herein, refer to sequence similarity between two polynucleotide sequences or between two polypeptide sequences, with identity being a more strict comparison. The phrases "percent identity or homology" and "identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences.

A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 70%, 75%, at least 80%, at least 85%, at least 90%, 91%, 92%, 93%, 94%, 95%, 96%, 97%, 98%, 99%, or more.

The degree of sequence identity is determined by choosing one sequence as the quesry sequence and aligning it with the internet-based tool ClustalW with homologous sequences taken from GenBank using the blastp algorithm (NCBI).

As is well known in the art, the genetic code is redundant in that certain amino acids are coded for by more than one nucleotide triplet (codon), and the invention includes those polynucleotide sequences which encode the same amino acids using a different codon from that specifically exemplified in the sequences herein. Such a polynucleotide sequence is referred to herein as an "equivalent" polynucleotide sequence. The present invention further includes variants of the hereinabove described polynucleotides which encode for fragments, such as part or all of the protein, analogs and derivatives of a polypeptide of SEQ ID NOS 1 to 37. The variant forms of the polynucleotide may be a naturally occurring allelic variant of the polynucleotide or a non-naturally occurring variant of the polynucleotide. For example, the variant in the nucleic acid may simply be a difference in codon sequence for the amino acid resulting from the degeneracy of the genetic code, or there may be deletion variants, substitution variants and addition or insertion variants. As known in the art, an allelic variant is an alternative form of a polynucleotide sequence, which may have a substitution, deletion or addition of one or more nucleotides that does not substantially alter the biological function of the encoded polypeptide.

The present invention further includes polypeptides, which have the deduced amino acid sequence of SEQ ID NOs 1 to 37, as well as fragments, analogs and derivatives of such polypeptides. The terms "fragment", "derivative" and "analog", when referring to a polypeptide of SEQ ID NOs 1 to 37, means polypeptides that retain essentially the same biological function or activity as a β-glucosidase. An analog might, for example, include a proprotein, which can be activated by cleavage of the proprotein portion to produce an active mature protein. The polypeptides of the present invention may be recombinant polypeptides, natural polypeptides or synthetic polypeptide.

The fragment, derivative or analog of a polypeptide of SEQ ID NOs 1 to 37, may be (i) one in which one or more of the amino acid residues is substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mature protein, such as a leader or secretory sequence or a sequence which is employed for purification, or for substrate or complex binding of the mature polypeptide or a proprotein sequence. Such fragments, derivatives and analogs are deemed to be within the scope of those skilled in the art to provide upon the basis of the teachings herein.

The polypeptides and polynucleotides of the present invention should be in an isolated form, and preferably they are purified to substantial homogeneity or purity. By substantial homogeneity is meant a purity of at least about 85%. In large scale or industrial applications their use in unpurified form is intended, preferably concentrated by removal of liquid.

The term "isolated" is used to mean that the material has been removed from its original environment (e. g., the natural environment if it is naturally occurring). For example, a naturally occurring polynucleotide or polypeptide present in a living organism is not considered to be isolated, but the same polynucleotide or polypeptide, when separated from substantially all of the coexisting materials in the natural system, is considered isolated. For DNA, the term includes, for example, a recombinant DNA which is incorporated into a vector, into an autonomously replicating plasmid or virus, or into the genomic DNA of a prokaryote or eukaryote; or which exists as a separate molecule (e. g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein. Further included is recombinant DNA which includes a portion of the nucleotides shown in one of SEQ ID NOs 38 to 43.

The polypeptides of the present invention include the polypeptides of SEQ ID NOS 1 to 37, as well as polypeptides which have at least 75% similarity (e. g. preferably at least 50%; and more preferably at least 70% identity) to a polypeptide of SEQ ID NOS 1 to 37, more preferably at least 85% similarity (e. g. preferably at least 70% identity) to a polypeptide of SEQ ID NOS 1 to 37, and most preferably at least 95% similarity (e. g. preferably at least 90% identity) to a polypeptide of SEQ ID NOS 1 to 37. Moreover, they should preferably include exact portions of such polypeptides containing a sequence of at least 30 amino acids, and more preferably at least 50 amino acids.

Fragments or portions of the polypeptides of the present invention may be employed as intermediates for producing the corresponding full-length polypeptides by peptide synthesis. Fragments or portions of the polynucleotides of the present invention may also be used to synthesize full-length polynucleotides of the present invention.

In a preferred embodiment of the invention, the nucleic acid is a polynucleotide, which has been codon-optimized for recombinant expression in a production host such as *E. coli Bacillus, Corynebacterium*, yeast, fungi or cell cultures, and which comprises, consists essentially of or consists of the nucleic acid sequence of SEQ ID NO: 38 or a nucleic acid that is at least 70% identical thereto.

Most preferably, the nucleic acid of the invention encodes for a mutant polypeptide of the invention, which contains at least one mutation selected from the mutations E40P, V111K, V293I, T423E and L441R and comprises, consists essentially of or consists of a nucleic acid sequence selected from the group consisting of SEQ ID NOs: 39-43 or a nucleic acid with at least 70% identity thereto:

| | |
|---|---|
| E40P; | SEQ ID NO: 39; |
| V111K; | SEQ ID NO: 40; |
| V293I; | SEQ ID NO: 41; |
| T423E; | SEQ ID NO: 42; and |
| L441R; | SEQ ID NO: 43. |

The present invention also includes vectors, which include such polynucleotides, host cells which are genetically engineered with such vectors and the production of polypeptides by recombinant techniques using the foregoing. Host cells are genetically engineered (transduced or transformed or transfected) with such vectors, which may be, for example, a cloning vector or an expression vector. The vector may be, for example, in the form of a plasmid, a conjugative plasmid, a viral particle, a phage, etc. The vector or the gene may be integrated into the chromosome at a specific or a not specified site. Methods for genome integration of recombinant DNA, such as homologous recombination or transposase-mediated integration, are well known in the art. The engineered host cells can be cultured in conventional nutrient media modified as appropriate for activating promoters, selecting transformants or amplifying the genes of the present invention. The culture conditions, such as temperature, pH and the like, are those commonly used with the host cell selected for expression, as well known to the ordinarily skilled artisan.

The polynucleotides of the present invention may be employed for producing polypeptides by recombinant techniques. Thus, for example, the polynucleotides may be included in any one of a variety of expression vectors for expressing polypeptides. Such vectors include chromosomal, nonchromosomal and synthetic DNA sequences, e. g., derivatives of SV40; bacterial plasmids; phage DNA; baculovirus; yeast plasmids; bacterial or yeast artificial chromosome (BAC, YAC); yeast episomal or integrative plasmids (YEps, YIps); *Agrobacterium tumefaciens* Ti plasmids; vectors derived from combinations of plasmids and phage DNA, viral DNA such as vaccinia, adenovirus, retrovirus, fowl pox virus, pseudorabies, M13 and Lambda. However, any other vector may be used as long as it is replicable and viable in the host, or can be used for genome integration.

The appropriate DNA sequence may be inserted into the vector by any of a variety of procedures. In general, the DNA sequence is inserted into an appropriate restriction endonuclease site(s) by procedures well known in the art, which procedures are deemed to be within the scope of those skilled in this art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac, ara, rha or trp, the phage lambda P.sub.L promoter and other promoters known to control expression of genes in prokaryotic or eukaryotic cells or their viruses.

The expression vector should also contain a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells, such as dihydrofolate reductase or neomycin-resistance for eukaryotic cell culture, or such as tetracycline-, kanamycin- or ampicillin-resistance in *E. coli*, or such as a counter selection marker like 5-fluorouracil, auxotrophies as lysine or histidine, or toxin/antitoxin like CcdB or MazF based selection for *Bacillus* species.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Streptomyces, Bacillus, Paenibacillus, Pseudomonas, Corynebacterium*; fungal cells, such as yeast (*Pichia, Saccharomyces, Kluyveromyces*) or basidiomycetes (*Trichoderma, Hypocrea, Aspergillus, Penicillium, Myceliopthora*); insect cells, such as *Drosophila* S2 and *Spodoptera* Sf9; animal cells, such as CHO, COS or Bowes melanoma; adenoviruses; plant cells, etc. The selection of an appropriate host is deemed to be within the scope of those skilled in the art from the teachings herein.

Synthetic production of nucleic acid sequences is well known in the art as is apparent from CLONTECH 95/96 Catalogue, pages 215-216, CLONTECH, 1020 East Meadow Circle, Palo Alto, Calif. 94303. Thus, the present invention also includes expression vectors useful for the production of the proteins of the present invention. The present invention further includes recombinant constructs comprising one or more of the sequences as broadly described above. The constructs may comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example: bacterial: pET21, pET24, pQE70, pQE60, pQE-9 (Qiagen), pBS, pD10, phagescript, psiX174, pbluescript SK, pbsks, pNH8A, pNH16a, pNHI8A, pNH46A (Stratagene), ptrc99a, pKK223-3, pKK233-3, pDR540 and pRIT5 (Pharmacia), pBE-S (TaKaRa-Bio Inc), pHT01, pHT43 (MoBiTec); and Eukaryotic: pWLNEO, pSV2CAT, pOG44, pXT1, pSG (Stratagene), pSVK3, pBPV, pMSG, and pSVL (Pharmacia). However, any other suitable plasmid or vector may be used as long as it is replicable and viable in the host.

Two appropriate vectors are pKK232-8 and pCM7. Particular named bacterial promoters include lacI, lacZ, T3, T7, gpt, lambda P.sub.R, P.sub.L, trp, ara, rha (*E. coli*), groESL and amyQ (*Bacillus*). Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Components of the expression vector may generally include: 1) a selection marker such as neomycin phosphotransferase (G418), hygromycin B phosphotransferase (hyg) or β-lactamase (bla) gene, 2) an origin of replication such as for *E. coli* and/or *Bacillus*, 3) a promoter such as a T7 and SP6 phage promoter sequence, 4) a regulatory operator such as a lac operator sequence, 5) a repressor such as the lactose operon repressor gene (lacIq) and 6) a multiple cloning site linker region. An origin of replication (oriC) may be derived from pBR322, pUC19 (LTI, Gaithersburg, Md.), pAM-beta1, pC194, pUB110, pBC16 (bacterial) or 2μ (yeast).

Particularly preferred vectors according to the invention include the pBEST vector (Promega), a vector of the pET vector series (Invitrogen) for *E. Coli*, the pHIS1525 or pC-Strep1622 vector for *Bacillus megaterium* (MoBiTec), the pBE-S vector for *Bacillus subtilis* (TaKaRa Bio Inc.), the pME18S-FL3 vector (GenBank Accession No. AB009864) for cultured cells, and the pM E18S vector (Mol. Cell Biol. 8:466-472 (1998)) for individual organisms. Preferred vectors for Gram-positive bacteria are selected from pTB19, pAM beta1, pLS32, pUB110, pC194, pBC16 and variants derived from them. Insertion of a nucleic acid of the present invention into vectors can be performed by standard methods such as ligase reactions using restriction enzyme sites (Current protocols in Molecular Biology edit. Ausubel et al. (1987) Publish, John Wiley & Sons, Section 11.4-11.11). Replication of the exogenous DNA may also be provided by integration into the host cell genome.

In a further embodiment, the present invention provides host cells containing the above-described constructs. The host cell can be a higher eukaryotic cell, such as a mammalian cell, or a lower eukaryotic cell, such as a yeast or a fungal cell, or the host cell can be a prokaryotic cell, such as a bacterial cell including Gram-positive or Gram-negative bacterial cells. Introduction of the construct into the host cell can be effected by calcium phosphate induced transfection, DEAE-Dextran mediated transfection, protoplast transformation, lipofection, cell competence, conjugation, transformation by viruses or electroporation (Davis, L., Dibner, M., Battey, I., Basic Methods in Molecular Biology, (1986); Grohmann, E., Muth, G., Expinosa, M., Microbiol. Mol. Biol. Rev., (2003)).

Such constructs in host cells are preferably used in a conventional manner to produce the gene product encoded by the recombinant sequence. Alternatively, the polypeptides of the invention can be synthetically produced by conventional peptide synthesizers or by chemical ligation of suitable fragments thus prepared.

Mature proteins can be expressed in mammalian cells, fungi, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Generally, recombinant expression vectors will include origins of replication and selectable markers permitting transformation of the host cell, e. g., the ampicillin resistance gene of *E. coli* and the *S. cerevisiae* TRP1 gene, and a promoter derived from a highly expressed gene to direct transcription of a downstream structural sequence. Such promoters can be derived from operons encoding glycolytic enzymes, such as 3-phosphoglycerate kinase (PGK), alpha-factor, acid phosphatase, or heat shock proteins, such as groESL, among others. The heterologous structural sequence is assembled in appropriate phase with translation initiation and termination sequences, and preferably, a leader sequence capable of directing secretion of translated protein into the periplasmic space or the extracellular medium. Optionally, the heterologous sequence can encode a fusion protein including an N-terminal identification peptide imparting desired characteristics, e.g., stabilization, simplified purification of expressed recombinant product or substrate binding. Commercially available vectors for fungal expression are pDEST-series (Invitrogen), pESC-series (Stratagene), pPIC-series (Invitrogen) and pRS-series (New England Biolabs) including promotors like GAL1, GAL10, ADH1 of *S. cerevisiae*, AOX1 of *P. pastoris*, cbhII of *T. reesei*, or gpdA of *A. nidulans* and selective auxotrophy markers like TRP1, HIS3, LEU2 or URA3.

Useful expression vectors for bacterial use are constructed by inserting a structural DNA sequence encoding a desired protein together with suitable translation initiation and termination signals in operable reading phase with a functional promoter which may be inducible in the respective host such as lac or ara promoters.

The vector will comprise one or more phenotypic selectable markers and one or more origins of replication to ensure maintenance of the vector and to, if desired, provide amplification within more than one hosts (shuttle vector). Suitable prokaryotic hosts for transformation include *E. coli*, *Bacillus subtilis*, *Bacillus licheniformis*, *Bacillus amyloliquefaciens*, *Bacillus macerans*, *Salmonella typhimurium* and various species within the genera *Bacillus*, *Corynebacterium*, *Paenibacillus*, *Pseudomonas*, *Streptomyces* and *Staphylococcus*, although others may also be employed as a matter of choice.

As a representative but non-limiting example, useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is induced by appropriate means (e. g., temperature shift or chemical induction), and cells are cultured for an additional period.

Cells are typically harvested by sedimentation in a centrifuge or by filtration, and then disrupted by physical or chemical means, with the resulting crude extract being retained for further purification. Secreted proteins may be harvested after applying or not applying osmotic shock, by centrifugation or filtration, optionally followed by concentration of the supernatant (containing the produced protein) by a suitable method such as ultrafiltration; such methods are well known to those skilled in the art.

Microbial cells employed in expression of proteins can be disrupted by any convenient method, including freeze-thaw cycling, sonication, mechanical disruption and use of cell-lysing agents; such methods are well known to those skilled in the art.

Preferred hosts according to the invention are industrial production organism/or cells such as filamentous fungi, yeast and bacteria as well as plant/animal cell cultures. More preferably prokaryotic hosts. Most preferably, the host according to the invention is a *Bacillus* strain, such as

*Bacillus amyloliquefaciens, Bacillus licheniformis, Bacillus macerans, Bacillus subtilis* or *Paenibacillus* sp.

The polypeptides can be recovered and purified from recombinant cell cultures by methods including salt (such as ammonium sulfate) or solvent (such as ethanol) precipitation, acid extraction, ultra-filtration, anion or cation exchange chromatography, phosphocellulose chromatography, hydrophobic interaction chromatography, size exclusion chromatography, affinity chromatography, hydroxylapatite chromatography, lectin chromatography and ultrafiltration. Recovery can be facilitated if the polypeptide is expressed at the surface of the cells or secreted to the periplasm (and released by osmotic shock) or outside of the cell, but such is not a prerequisite. Recovery may also be desirable of cleavage products that are cleaved following expression of a longer form of the polypeptide. Such cleavage can occur spontaneously either by an autocatalytic process or by enzymes produced in the host. Alternatively the preprotein can be cleaved artificially by adding a processing enzyme such as a protease which may act on a native or an artificially introduced processing site. Protein refolding steps as known in this art can be used, as necessary, to complete configuration of the mature protein. High performance liquid chromatography (HPLC) can be employed for final purification steps. In special cases purification may not be necessary.

The polypeptides of the present invention may be produced by recombinant techniques from a prokaryotic or eukaryotic host (for example, by bacterial, fungal, yeast, higher plant, insect or mammalian cells in culture). Depending upon the host employed in a recombinant production procedure, the polypeptides of the present invention may be glycosylated or may be non-glycosylated. Polypeptides of the invention may also include an initial methionine amino acid residue, which may be cleaved off by the host.

When the polypeptides of the present invention are secreted into the culture media, the polypeptides produced by the above-mentioned method can be harvested by collecting the media, separating the cells by centrifugation, filtration or other means of cell separation. When the polypeptides of the present invention are produced inside cells, first, the cells are lysed, and then these polypeptides are collected, preferably after removing intact cells and cell debris by centrifugation or filtration.

In a preferred embodiment, the proteins of the invention are isolated and purified so as to be substantially free of contamination from other proteins. For example, the proteins of the invention should constitute at least 80% by weight of the total protein present in a sample, more preferably at least 90%, even more preferably at least 95%, and most preferably at least 98% by weight of the total protein. In another preferred embodiment the protein is used unpurified, for example by separating the cells and using the secreted protein with the culture supernatant directly without further purification. In still another preferred embodiment the proteins of the invention in the clarified culture supernatant is concentrated by convenient methods such as ultrafiltration.

These proteins may be in the form of a solution in water, another suitable solvent, such as dimethyl sulphoxide (DMSO) or ethanol, or a mixture of suitable solvents.

Examples of mixtures of solvents include 10% (by weight) ethanol in water and 2% (by weight) DMSO in water. A solution may further comprise salts, buffering agents, chaotropic agents, detergents, preservatives, anti-freezing agents and the like. Alternatively, the proteins may be in the form of a solid, such as a lyophilized, freeze-dried or spray-dried powder or a crystalline solid, which may also comprise a residual solvent, a salt or the like.

In a further embodiment, the invention provides the use of the mutant polypeptides of SEQ ID NOs: 1 to 37 in cellulosic technology.

"Cellulosic technology" is a set of technologies to convert nonfood biomass, such as wood, straw, energy grasses, food processing residues or waste paper, to biosugars such as glucose and xylose. Cellulosic technologies encompass all the aspects of making biofuels, solvents and renewable commodity chemicals from cellulosic biomass. Such technologies include enzyme manufacture, biomass pretreatment, cellulose and hemicellulose hydrolysis, and lignin combustion or conversion and may include biorefinery technologies. Two major types of cellulosic solvent technology are 1) gasification of biomass to synthesis gas and resynthesis of larger molecules like ethanol, and
2) enzymatic hydrolysis of cellulose and hemicellulose to component sugars, followed by fermentation or chemical conversion to cellulosic ethanol or other advanced biofuels.

Gasification methods have the advantage of being fast and relatively less sensitive to feedstock type, but the disadvantage of destroying useful structures like the glucose molecule.

Enzymatic methods are slower, but produce monomeric sugars such as glucose or xylose, which are the substrate of choice for metabolic or chemical conversion for producing ethanol, butanol, renewable diesel, renewable jet fuel, and a wide variety of useful biobased chemicals as industrial feedstocks for bioplastics, renewable chemicals and solvents.

The mutant polypeptides of the present invention are particularly useful in enzymatic methods of cellulosic technology, either mixed as soluble enzymes to a soluble or complexed mixture of biomass depolymerizing enzymes (such as cellulases or hemicellulases), or as a component integrated into an enzyme complex by attaching a polypeptide module for complex binding such as a dockerin which bind to the cohesin of a complex-backbone scaffold.

The mutant polypeptide of the invention converts cellobiose to glucose. Glucose is an universal substrate for industrial fermentations, allowing production of a wide variety of renewable chemicals and bioplastics. This glucose is also the substrate for production of cellulosic ethanol, chemical commodities and advanced biofuels such as green gasoline, green diesel, butanol and biojetfuel.

By providing cheap sugars from nonfood biomass, the mutant polypeptides of the invention enable production of precursors of bioplastics, biochemicals and biofuels without the use of fossil oil or grain, starch, palm oil and other food-byproducts. Nonfood biomass has a lower $CO_2$ footprint compared to food biomass and an even more reduced $CO_2$ footprint as compared to fossil oil.

In a further embodiment, the invention provides the use of the mutant polypeptides of SEQ ID NOs: 1 to 37 as cellulolytic enhancers.

The mutant polypeptides of the invention are particularly suitable for use in methods for degrading or converting a cellulosic material, comprising: treating the cellulosic material with an effective amount of one or more cellulolytic proteins, such as one or more cellulases or hemicellulases, in the presence of an effective amount of a mutant polypeptide of the invention. The mutant polypeptides of the invention have a cellulolytic enhancing activity and increase the degradation of cellulosic material compared to the absence of the mutant polypeptide of the invention. By using the mutant polypeptides of the invention, it is possible to perform the methods for degrading or converting a cellulosic material at an increased temperature compared to conventional methods or processes. Suitably, the methods for degrading or converting a cellulosic material in the presence of at least one mutant polypeptide of the invention can be performed at a temperature of >60° C., more suitably at a temperature of 61° C., 62° C., 63° C. or 64° C., most suitably at a temperature of 65° C., or at a higher temperature. Performing the methods for degrading or converting a cellulosic material at temperatures higher than 60° C. has several advantages. The risk for contaminations can be effectively minimized and the solubilization of the cellulose microcrystals is improved significantly, thereby making the bulk part of the cellulose better available as a substrate for the cellulases used in the processes. The mutant β-glucosidase polypeptide of the present invention can in these processes be used to effectively degrade cellobiose and cellodextrins, which are the resulting product of the degradation of cellulose by the cellulases, to glucose monomers, thereby preventing the end product inhibition of the cellulases by cellobiose. A further advantage of the mutant β-glucosidase polypeptides of the invention is that they show a very low feedback inhibition even by higher concentrations of glucose, in particular at process temperatures higher than 60° C., most particularly higher at a temperature of 65° C.

The mutant enzyme can furtheron be used in industrial chemical processes of modifying glycosylated compounds. An example is its action on naringin, the bitter substance in citrus fruits. β-Glucosidase debitters fruit juices and can be used in conjunction with a thermostable α-rhamnosidase in industrial processes (Puri et al. 2011).

The mutant polypeptides of the invention can be further used as part of artificial cellulosomes. Artificial cellulosomes are described e.g. in EP2410061 and WO2012010295.

An artificial cellulosome is for example a complex comprising:
a) a backbone scaffold comprising at least four binding sites, wherein at least two of the binding sites have essentially the same binding specificity; and
b) an enzyme component bound to each of said four binding sites, wherein at least three of said enzyme components are different enzyme components.

The backbone scaffold may be a linear, synthetic or biological backbone.

Typically, the backbone scaffold has at least four cohesin binding sites for dockerins.

In the artificial cellulosome, the backbone scaffold suitably consists of one or more proteins, wherein the one or more proteins are linked together by chemical interaction or by a cohesin-dockerin interaction, whereby the binding specificity of the linking interaction is different from the binding specificity of the enzymes.

The backbone scaffold may be derived from a non-catalytic scaffolding protein from cellulolytic, cellulosome forming microorganisms or genetically modified derivatives thereof. Preferably, the backbone scaffold is derived from the non-catalytic scaffolding protein CipA from *Clostridium thermocellum* or genetically modified derivatives thereof.

The backbone scaffold in said artificial cellulosome further may comprise a carbohydrate binding module (CBM). Preferably, said carbohydrate binding module is a carbohydrate binding module (CBM3) from the cipA gene of *Clostridium thermocellum* that is integrated into or attached to the linear backbone scaffold.

The enzyme components of said artificial cellulosome comprise a dockerin module and a catalytic module of an enzyme. Suitably, the enzyme components are selected from the group consisting of: processive or non-processive endo-β-1,4-glucanases, processive exo-β-1,4-glucanases and glucosidases from polysaccharolytic microorganisms or genetically modified derivatives thereof. In a preferred embodiment, the enzyme components are derived from dockerin module containing components of the *Clostridium thermocellum* cellulosome or from non-cellulosomal components of *Clostridium thermocellum* having a dockerin module fused thereto. More preferably, the enzyme components comprise CelK-d1, CelR-d1 CelT-d1, CelE-d1, CelS-d1 and BglB-d1 as disclosed in EP2410061, or derivatives thereof having more than 50% amino acid sequence identity in their dockerin modules. Most preferably, at least one of the mutant β-glucosidase polypeptides of the present invention is comprised in said artificial cellulosomes. Particularly preferred for use in these artificial cellulosomes are the mutant poylpeptides of SEQ ID NOs: 1 to 37, optionally containing a dockerin module fused thereto. The mutant β-glucosidases of SEQ ID NOs: 1 to 37 may also be added as a soluble protein and not bound to the complex.

EP2410061 discloses also a method for preparing an artificial cellulosome. Such method suitably comprises the steps of:
a) recombinantly producing the enzyme components of the complex or cellulosome,
b) recombinantly producing the backbone scaffold as described above,
c) mixing the purified, partially purified or non-purified components of a) and b); and
d) randomly binding the enzyme components to the backbone scaffold.

Suitably, the total amount of backbone scaffolds in step c) and the total amount of enzyme components are mixed together in a molar ratio of 1 cohesin module to 1 enzyme component, and the at least three enzyme components are mixed together in a molar ratio of 1:1 to 1:15 to each other.

The invention further relates to a method for enzymatic hydrolysis of cellulosic substrates comprising the steps of:
a) mixing at least one mutant polypeptide of the invention or the complex containing at least one mutant polypeptide of the invention with cellulosic biomass or insoluble cellulose;
b) enzymatically hydrolyzing cellulosic biomass or insoluble cellulose under thermophilic conditions; and optionally
c1) isolating the degradation products; and/or
c2) further processing the degradation products.

Further processing of the degradation products means to, e.g. produce a biological a chemical or solvent, such as a fuel or generate electricity or produce bioplastics or bio-chemicals.

"Thermophilic conditions" means a process temperature above 60° C., preferably 65° C., or probably higher.

The invention further provides the use of the complex or the artificial cellulosome, any of which comprising at least one mutant polypeptide selected from SEQ ID NOs 1 to 37 of the present invention, for enzymatic hydrolysis of cellulosic biomass or insoluble cellulose, preferably of crystalline cellulose or a crystalline cellulose containing substrate.

The invention further relates to a composition comprising the mutant polypeptide according to one of SEQ ID NOs: 1 to 37 or the artificial cellulosome comprising at least one mutant polypeptide according to one of SEQ ID NOs: 1 to 37. Such composition may comprise the complex or the mutant polypeptide of the invention, cellulosic biomass or insoluble cellulose and water. Preferably, said composition is adjusted to an optimal or near optimal pH of 6.5±0.5.

Moreover, the β-glucosidase gene cglT coding for a mutant polypeptide according to one of SEQ ID NOs: 1 to 37 may be C-terminally fused to a dockerin type I from an enzyme component of the C. thermocellum cellulosome by genetic engineering, using a short linker sequence, for instance a linker sequence rich in proline, threonine and serine residues (PTS-linker). This fused enzyme CglT-docI can be recombinantly produced in E. coli and purified by His-tag affinity chromatography. The purified enzyme shows binding to all cohesins of the C. thermocellum backbone scaffold CipA, i.e. a mixture of 8 mole CglT-docI with 1 mole CipA (containing 8 cohesin cohI binding sites) shows a complete binding without free CipA or CglT-docI. The bound enzyme is fully active on cellobiose.

In contrast to the prior art (e.g. WO2013114362), using a dockerin type II for fusion with the β-glucosidase, the amount of β-glucosidase in an artificial complex, i.e. the ratio of cellulases to β-glucosidase can be selected freely. In WO2013114362, 1 molecule of β-glucosidase-docII per molecule of backbone scaffold has to be used, because the backbone scaffold contains only one binding site (cohII) for binding the docII of the fusion protein—docII does not bind to cohI (Carvalho et al. 2005).

The advantage of binding the β-glucosidase is that the complex contains a β-glucosidase tightly bound to it, so that the β-glucosidase can for example be separated from the reaction mix together with the cellulases and is not lost. Moreover the β-glucosidase is spacially close to the cellulases which produce the cellobiose and hence its local concentration on the β-glucosidase substrate (cellulose-derived cellobiose) is higher, making less enzyme sufficient for full reaction.

In another preferred embodiment of the invention the mutant polypeptide of the invention is used as soluble enzyme solely or in combination with other enzymes method for enzymatic hydrolysis of cellulosic substrates.

Figure 5:
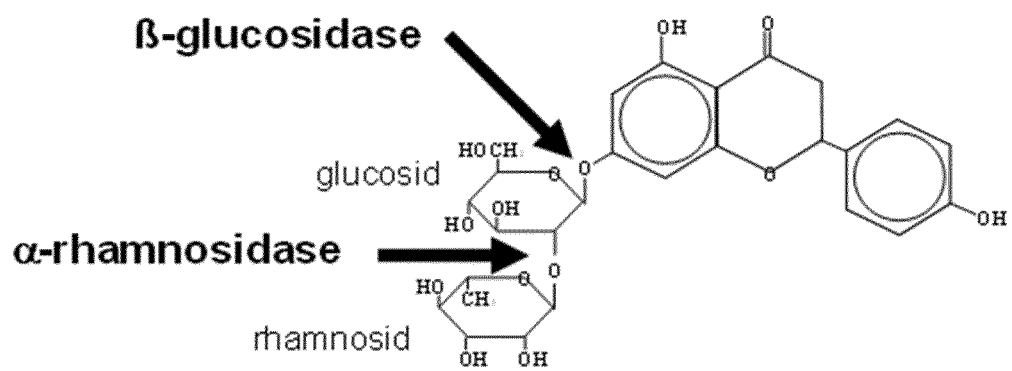
FIG. 5: Chemical structure of naringin. The glycosylation by rhamnosidic and glucosidic residues is indicated, as are the points of hydrolysis by rhamnosidase and glucosidase respectively.

The mutant polypeptides according to SEQ ID NOs: 1 to 37 can be used to modify small molecules. Many small molecules such as flavonoids are glycosylated in nature. β-Glucosidase can split off glucosidic side chains and thereby modifying the chemical nature of these molecules dramatically. An example is naringin, the major bittering substances of citrus fruit juices (Kaur et al. 2010) (see FIG. 5). It could be shown that a combination of an α-rhamnosidase with a β-glucosidase (also called naringinase in the literature) from the thermophilic, anaerobic bacterium Clostridium stercorarium—which is closely related to T. brockii—can effectively convert the bitter tasting naringin to the non-bitter unglycosylated flavonoid naringenin, i.e. 4,5,7-trihydroxy flavonone (Zverlov et al. 2000).

TABLE 2

Degradation of naringin with rhamnosidase A (Ram), β-glucosidase (Bgl) or a mixture of both (presence of enzyme indicated by + and −). The interpretation of the results is indicated in the right column. Numbers indicate the relative molar concentration of the respective reaction products. Prunin: glycosylated flavonoid (NaOH is added for photometric determination of naringenin naringin and prunin); PGO, glucose assay with glucose oxidase (Sigma-Aldrich); DNSA (dinitrosalicylic acid assay), assay of reducing ends of liberated rhamnose and glucose.

| Naringin incubation with enzyme | | Relative concentration | | | | Interpret. Reaction end |
|---|---|---|---|---|---|---|
| Ram | Bgl | naringenin OD310 NaOH | naringin + prunin OD375 NaOH | glucose OD590 PGO | reduc. sugar OD492 DNSA | products |
| − | − | 0 | 1 | 0 | 0 | no hydrolysis |
| + | − | 0 | 1 | 0 | 0.6 | prunin + rhamnose |
| − | + | 0 | 1 | 0 | 0 | no hydrolysis |
| + | + | 1 | 0 | 1 | 1.0 | naringenin + rhamnose + glucose |

This reaction shows an example for the use of β-glucosidase for deglycosylation in biotechnology and in an industrial application (Puri et al. 2005; Puri 2000). Thus, in a further embodiment, the invention provides the use of the mutant polypeptides according to SEQ ID NOs: 1 to 37 in processes for modification of small molecules, e.g. in food industry.

The invention is further illustrated by the following examples and figures.

EXAMPLES OF THE INVENTION

Example 1

Isolation of the cglT Wild Type Gene

The complete gene cglT from Thermoanaerobacter brockii was synthesized in the codon-usage of E. coli and was cloned into the pET24a(+) expression vector (Novagen, Germany) and thereby fused to a C-terminal His-Tag. E. coli DH10B cells (Invitrogen, USAPlasmid DNA was isolated and transformed for recombinant protein expression into E. coli BL21 Star™ (DE3) cells (Invitrogen, USA). Cells were grown in LB medium containing 100 µg/ml ampicillin (w/v) and incubated at 37° C. Liquid cultures (the same medium) were shaken at 37° C. with 180 rpm in a rotary shaker. LB medium contained yeast extract 5 g, Trypton 10 g, NaCl 10 g per liter double distilled water; NaOH was added to adjust the pH to 7.2. 16 g/l agar-agar was added to solidify the medium.

Example 2

Mutagenesis of the cglT Wild Type Gene

Point mutations of the cglT wild type gene leading to potentially stabilizing amino acid exchanges were introduced into the wild type cglT gene by site directed mutagenesis with PCR, using pairs of synthesized oligonucleotides harboring appropriate mismatches (table 1).

TABLE 1

Mutagenesis primers used:

| Primer | Sequence (5'→3') | Mutation | SEQ ID NO: |
|---|---|---|---|
| V111K_neu | AGCGCGATATTAAACCCGCAGCGA CCATTTATC | V111K | 45 |
| V111K_rev_neu | GATAAATGGTCGCTGCGGGTTTAA TATCGCGCT | | 46 |
| V293I | CGATTGACTTCTTAGGCATCAATTA CTACACTC | V293I | 47 |
| V293I_rev | GAGTGTAGTAATTGATGCCTAAGA AGTCAATCG | | 48 |
| T423E | ATTGTGTATGTGGACTATGAGACC CAGAAACG | T423E | 49 |
| T423E_rev | CGTTTCTGGGTCTCATAGTCCACAT ACACAAT | | 50 |
| L441R | ACAAAGAGGTGATTCGCGATGATG GGATTGAAG | L441R | 51 |
| L441R_rev | CTTCAATCCCATCATCGCGAATCA CCTCTTTGT | | 52 |

Due to the mismatches, the respective codons were modified during the PCR reactions and the respective amino acid substitutions in the target proteins were achieved thereby.

The thermal cycling parameters for the PCR reaction were: 98° C. for 3 min; 20 cycles at 98° C. for 10 s, 65° C. for 45 s and 72° C. for 105 s, followed by a final extension at 72° C. for 5 min, using Phusion HF as DNA polymerase (New England Biolabs, USA). To remove template plasmid DNA containing unmodified cglT DNA, the PCR product was treated with 10 U of enzyme DpnI (New England Biolabs, USA) for 3 h at 37° C. and subsequently purified with the QIAquick PCR Purification Kit (Qiagen, Germany). After the transformation of chemically competent E. coli DH10B cells with this DNA, plasmids were harvested from overnight cultures in LB medium with the QiaPrep Spin Miniprep Kit (Qiagen, Germany) and sequenced, to identify successful nucleotide base exchanges and the correct sequence.

Example 3

Recombinant Expression of the Mutant Polypeptides

Plasmids harboring the wild type and the mutated β-glucosidase genes were transformed into chemically competent E. coli BL21 Star™ (DE3) cells for protein expression. Precultures were prepared from single colonies in liquid LB medium. After growth for 6-8 h under aeration, the expression culture was prepared by inoculating ZYP 5052 auto-induction medium containing 2 g/l lactose and the culture was incubated overnight [Studier, F. W., Protein production by auto-induction in high density shaking cultures. Protein Expr Purif, 2005. 41: 207-34.2]. Cells were harvested by centrifugation (4500 rpm, 10 min, 4° C.) and the pellets were frozen at –20° C. until further usage. To lyse the cells, pellets were thawed on ice, resuspended in cell lysis buffer (50 mM MOPS pH 7.3, 0.5 M NaCl, 20 mM imidazole, 20 mM $CaCl_2$), supplemented with protease inhibitor cocktail (cOmplete, Mini, EDTA-free; Hoffmann-La Roche AG, Switzerland) and lysozyme (100 mg/ml; AppliChem GmbH, Germany) and incubated on ice for 30 min. The cells were then disrupted by sonication, controlling the cell disruption microscopically at intervals.

After removal of cellular debris by centrifugation (18,000 rpm, 20 min, 4° C.), the recombinant proteins were purified from the supernatant by affinity chromatography, employing $Ni^{2+}$-NTA columns (HisTrap FF, GE Healthcare, GB) embedded in an ÄKTApurifier system (GE Healthcare, Sweden) in accordance with the methods of the supplier. Recombinant proteins were eluted with elution buffer (50 mM MOPS pH 7.3, 0.5 M NaCl, 0.5 M imidazole, 20 mM $CaCl_2$) and further enriched by denaturation of contaminating E. coli proteins (60° C., 15 min), followed by centrifugation (15,000 rpm, 15 min, 4° C.). Purity and expected protein size (ca. 53 kDa) of CglT and its mutants was subsequently verified by SDS-PAGE on 10% polyacrylamide gel electrophoresis after staining with Coomassie Blue. Protein concentration was determined by measuring the absorbance at 280 nm, taking into account the individual amino acid composition of the proteins using the Protparam tool (http://web.expasy.org/protparam/). Enzyme aliquots were then stored frozen (at –20° C.) until further usage, with 20% (v/v) glycerol and 0.02% sodium azide as stabilizer.

Example 4

Determination of the Enzymatic Activity of the Mutant Polypeptides

Enzymatic activity of β-glucosidase enzyme was assayed at 60° C. in a MOPS buffer system (100 mM MOPS, pH 6.5, 50 mM NaCl, 10 mM $CaCl_2$), using the chromogenic substrate p-nitrophenyl-β-D-glucoside (20 mM) as substrate in a 500 µl reaction volume. A mild reducing agent may be added, such as TCEP (tris(2-carboxyethyl)phosphine hydrochloride) (Sigma-Aldrich). After an appropriate incubation time, the reaction was stopped by adding 1 ml of 1 M $NaHCO_3$ on ice. A potential precipitate was removed by centrifugation (13,000 rpm, 10 min). The amount of released p-nitrophenol (p-NP) was calculated from the absorbance at 395 nm ($A_{395}$) using the following equation, the formula of which has been derived from a calibration curve and contained all necessary parameters:

$n(p\text{-}NP) = A_{395} \times 0.093$ µmol.

Specific enzymatic activity in [U/mg] was calculated by calculating n (p-NP) with the amount of enzyme utilized in the assay and the reaction time, respectively. All measurements were carried out in triplicate.

Results

The investigated CglT mutant variants (V111K, V293I, T423E and L441R) showed an increase in the specific enzyme activity by 30-90% compared to the wild type (CglT wt) enzyme. Because of the always higher specific enzyme activity compared to the wild type, the mutant polypeptides are much more suitable for use in processes for the enzymatic hydrolysis of cellulosic biomass or other applications than the wild type enzyme.

Example 5

Determination of the Thermostability of the Mutant Polypeptides

The thermostability of the recombinant mutant polypeptides was performed as follows: Concentrated enzyme solutions (3.4-4.3 mg/ml) were incubated for 48 h at 65° C. Samples of 10 µl were taken at the time points 0 hour and 48 hours. Immediately after obtaining the sample, it was diluted appropriately and the specific activity of the mutant polypeptides was measured in an enzyme assay, based on the model substrate p-nitrophenyl-β-D-glucopyranoside (20 mM), as described above (with 30 min incubation time at 60° C.).

Results

Figure 2:
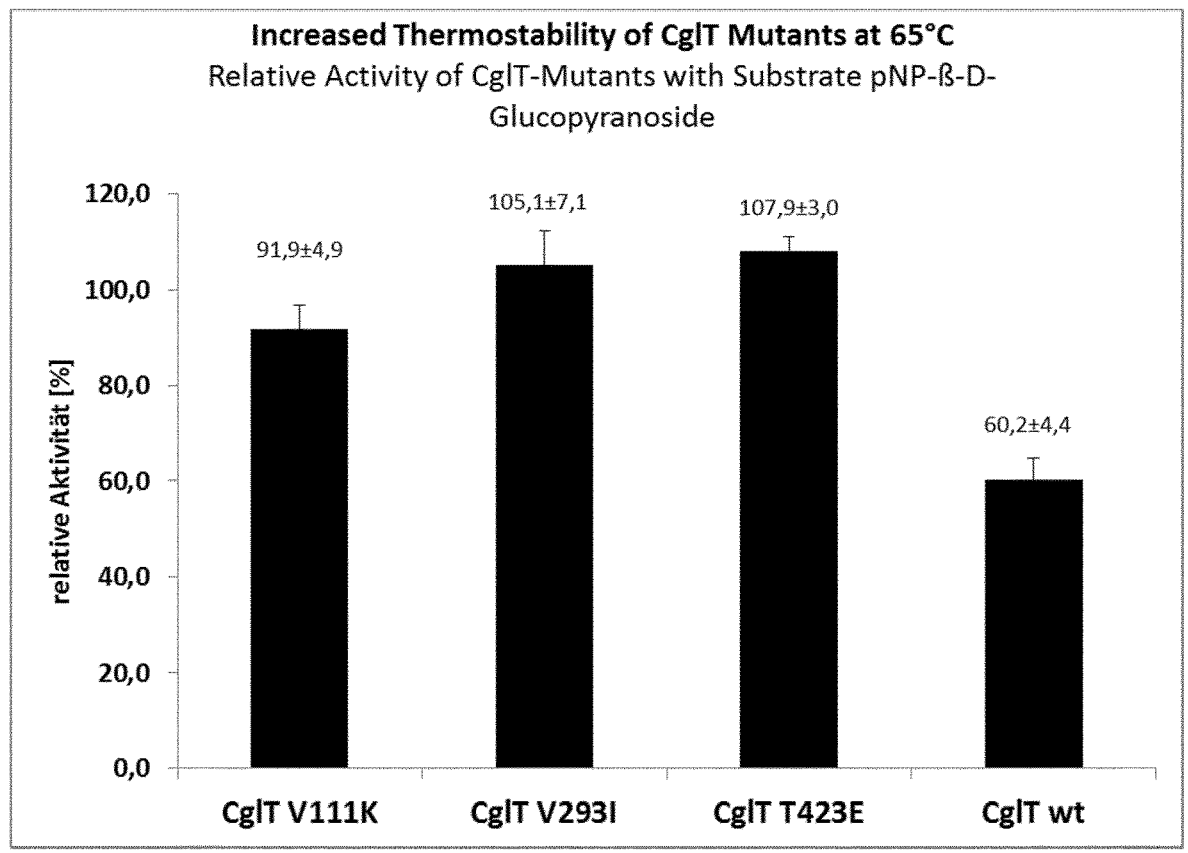
FIG. 2 shows the relative enzyme activity of the wild type enzyme (right) and of the CglT-mutants V111K, V293I and T423E (from left to right) after incubation for 48 h at 65° C. relative to the enzyme activity without prior incubation, using 20 mM substrate p-NPG (p-nitrophenyl-β-D-glycoside). Reaction conditions of the assay: 60° C., 6 ng enzyme, 1×MOPS buffer, reaction time 30 min. Incubation conditions: 65° C., 3.4-4.3 mg/ml enzyme in 400 mM imidazole, 240 mM NaCl, 80 mM MOPS pH 7.0, 8 mM $CaCl_2$ and 20% (v/v) glycerol. Determinations were performed in triplicate.

The investigated CglT mutant variants (V111K, V293I and T423E) showed an improved thermostability under the tested conditions. The relative activity of the mutant variants was within 48 hours not (V293I and T423E) or only slightly (V111K) decreased, relative to the enzyme activity without incubation whereas the CglT wildtype showed only 60% of the initial activity (FIG. 2).

Usually, the process duration of the enzymatic hydrolyses of cellulosic substrates or cellulosic biomass does not exceed 48 hours.

Example 6

Hydrolysis of Cellobiose

The hydrolytic activity on cellobiose, the end product of soluble or complexed cellulases on cellulose, was estimated for the purified enzyme variants in a 500 µl reaction batch containing 0.5% cellobiose in a MOPS buffered solution (100 mM MOPS, pH 6.5, 50 mM NaCl, 10 mM CaCl$_2$) applying 200 ng enzyme. The batch was incubated at 60° C. for 1 h and the hydrolysis stopped by boiling at 100° C. for up to 30 min. After the solutions had been de-salted with half the volume of ion-exchange beads (Dowex-1 Strongly Basic Anion Exchange Resin, Sigma-Aldrich, USA). the reaction products were analyzed by thin layer chromatography: 1 µl sample was spotted on a TLC plate (TLC Silica gel 60, Merck KGaA, Germany) and separated with a liquid phase of 80% acetonitrile in water. The products were visualized with a vaporized staining solution containing aniline, diphenylamine, and orthophosphoric acid in acetone (1:1:8) and incubation at 130° C. for 15 min (see FIG. 3).

Figure 3:
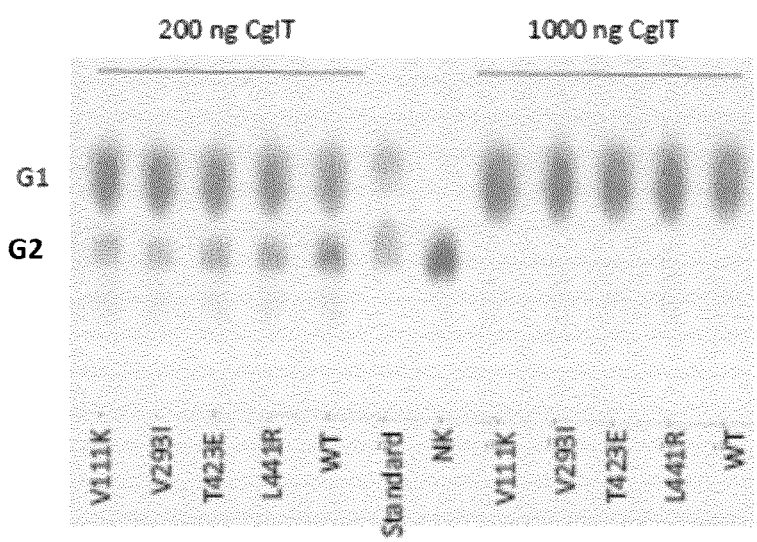
FIG. 3 shows the comparison of the enzymatic hydrolysis of cellobiose by the CglT-mutants and by the wild type enzyme (WT) at a substrate concentration of 0.5% (w/v). A reaction sample without enzyme was used as negative control (NK). Standard used: 1 μl of a 0.1% (w/v) mixture of saccharides; G1=glucose, G2=cellobiose. Sample volume used in the thin layer chromatography: 1 μl. Running buffer: 80% (v/v) acetonitrile in $H_2O$. The left hand side of the thin layer plate shows the degradation of cellobiose using 200 ng enzyme/sample. The right hand side shows the degradation of cellobiose using 1 μg enzyme/sample. Negative control: NK, sample without enzyme.

It was shown, that the CglT-mutant polypeptides were at relatively low enzyme concentrations (200 ng/sample) more effective in the degradation of cellobiose to glucose than the wild type enzyme (FIG. 3). The reaction time was 1 hour. At higher enzyme concentrations (1 µg/sample) the cellobiose was completely degraded by all CglT variants (not shown).

Figure 4:
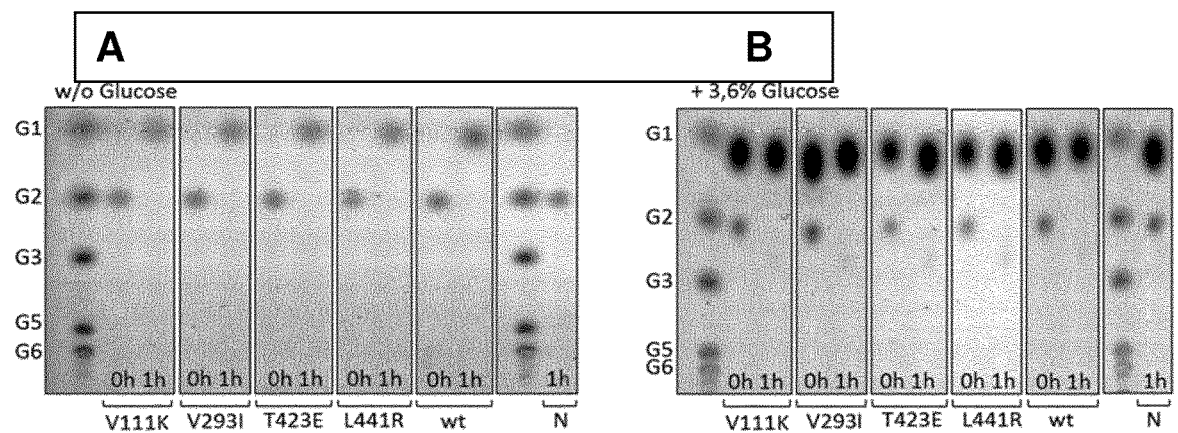
FIG. 4 Cellobiose hydrolysis by the wild type enzyme and the CglT-mutants V111K, V293I, T423E and L441R (from left to right). 0.5% (w/v) cellobiose were incubated in the absence (A) and presence of 3.6% (w/v) glucose (B) to test for end product inhibition. Negative control (N) is the same reaction without enzyme. Standard (S): 1 μl of 0.1% (w/v) mixture of cellodextrins G1-G6 (G4 missing). Volume applied was 0.25 μl. Eluent was 80% (v/v) acetonitril in $H_2O$.

Further investigations in regard to the end product inhibition using the mutant polypeptides, showed that, also in presence of 14% glucose (w/v), cellobiose was hydrolyzed completely (see FIG. 4).

These results show, that the thermostability of the CglT-mutants, the feedback inhibition and the specific activity could be optimized compared to the wild type enzyme. A further advantage thereof is, that the optimized mutant enzyme variants can be used more flexibly, i.e. can be adapted to desired reaction conditions for the enzymatic hydrolysis of cellulosic biomass.

Example 7

Degradation of Cellulase Reaction-Products

Figure 6:
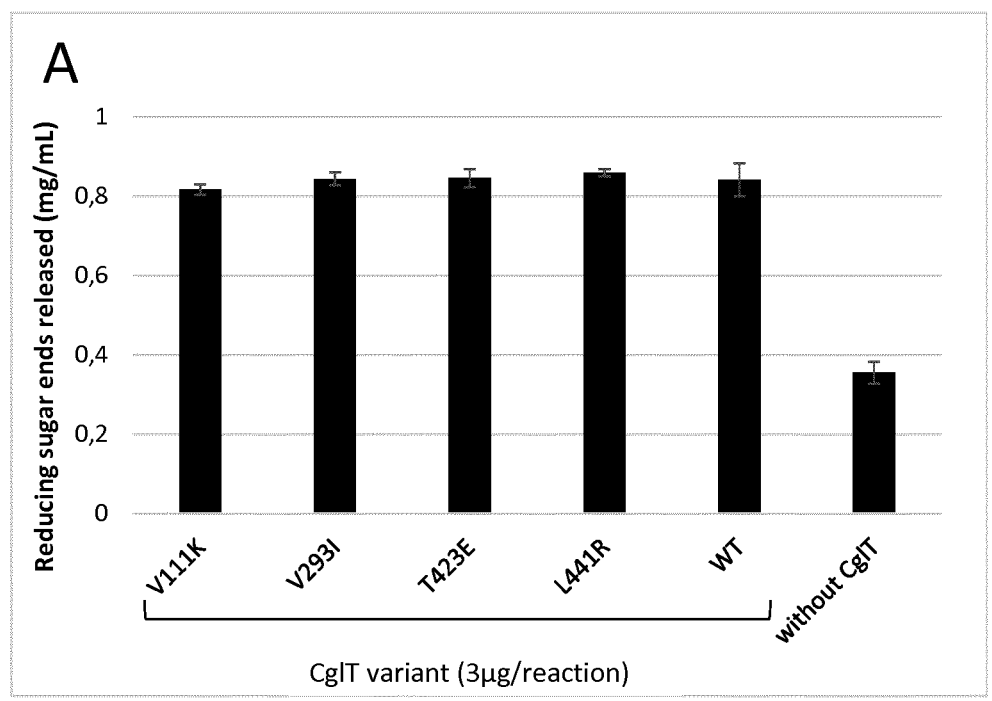
FIG. 6: Addition of CglT enhances cellulase activity. CglT wild type protein and variants thereof were added to reactions of a *C. thermocellum* cellulosome preparation. Products were quantitatively (A: determination of reducing sugars) and qualitatively (B: thin layer chromatography of reaction products) assayed. Assay conditions were: hydrolysis in 1× reaction buffer (0.1 M MOPS, 50 mM NaCl, 10 mM $CaCl_2$, pH 5.8; process temperature 60° C., pH 6.5 at RT) containing 2 mM TCEP and 1 μg native cellulosome supplemented with or without 3 μg CglT β-Glucosidase (WT and mutational variants) on 0.25% Avicel as the insoluble substrate. Reaction volume: 200 μL, reaction time: 36 hours. M1-1 (glucose) and C2 (cellobiose) as standard. M1-5: C1 to C5 as standard.
Figure 6:
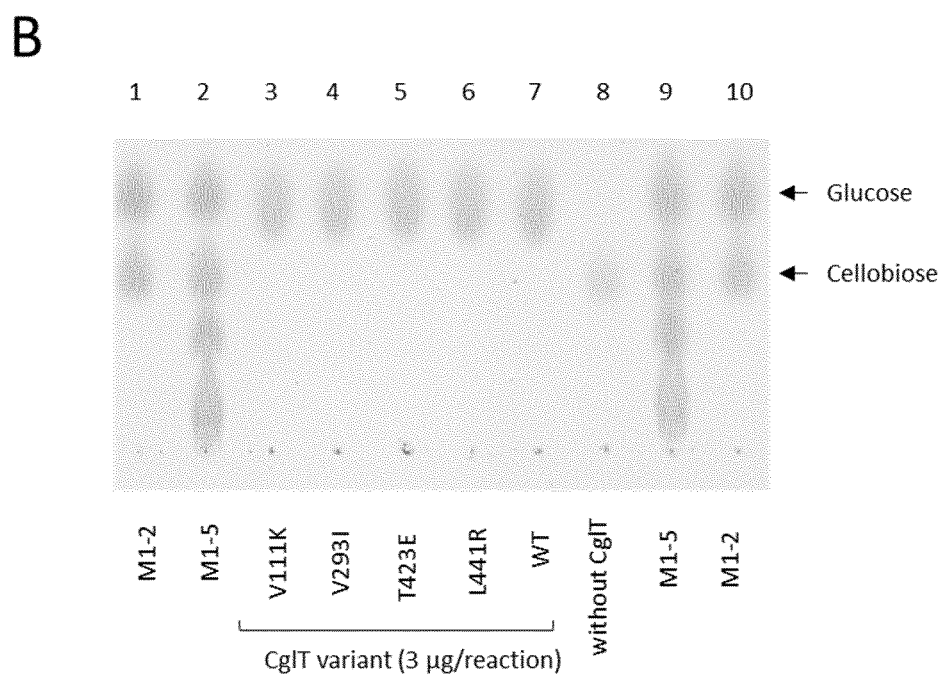

Cellulosomes were prepared from a *C. thermocellum* culture by gel-filtration chromatography of the culture supernatant and collecting the high molecular weight fraction. Aliquots of the cellulosome preparation were added to a suspension of 0.25% (w/v) microcrystalline cellulose (Avicel, Sigma-Aldrich) and hydrolysed in 1× reaction buffer (0.1 M MOPS, 50 mM NaCl, 10 mM CaCl$_2$, pH 5.83 at process temperature of 60° C.). Mixtures were supplemented or not supplemented (as indicated in FIG. 6) with 3 µg CglT (WT and mutational variants). Reaction volume was 200 µL, the reaction time 36 hours.

Released sugars were determined by assaying the amount of reducing ends with the DNSA reagent (FIG. 6, A). Whereas without β-glucosidase 0.35 mg/ml reducing sugars were released (as glucose equivalents), after addition of β-glucosidase the amount of reducing was enhanced to 0.82 mg/ml and thus more than doubled. The unexpected amount of activity gain by addition of β-glucosidase was assumed to be the result of diminishing the end-product inhibition by the cellobiose released by the cellulosomal cellulases which are inhibitory especially for exo-glucanases (cellobiohydrolases).

FIG. 6B shows the cellobiose released from the crystalline cellulose (Avicel) in the lane "without CglT". This cellobiose product is completely degraded to glucose by the addition of CglT or its mutant variants.

LITERATURE

Anbar, M.; Lamed, R.; Bayer, E. A. (2010): Thermostability Enhancement of *Clostridium thermocellum* Cellulosomal Endoglucanase Cel8A by a Single Glycine Substitution. In: *ChemCatChem* 2 (8), pp. 997-1003. DOI: 10.1002/cctc.201000112.

Breves, R.; Bronnenmeier, K.; Wild, N.; Lottspeich, F.; Staudenbauer, W. L.; Hofemeister, J. (1997): Genes encoding two different beta-glucosidases of *Thermoanaerobacter brockii* are clustered in a common operon. In: *Applied and environmental microbiology* 63 (10), pp. 3902-3910.

Carvalho, A. L.; Pires, V. M.; Gloster, T. M.; Turkenburg, J. P.; Prates J. A.; Ferreira, L. M.; Romão, M. J.; Davies, G. J.; Fontes, C. M.; Gilbert, H. J. (2005): Insights into the structural determinants of cohesin-dockerin specificity revealed by the crystal structure of the type II cohesin from *Clostridium thermocellum* SdbA. J Mol Biol. 349:909-15

Gefen, G.; Anbar, M.; Morag, E.; Lamed, R.; Bayer, E. A. (2012): Enhanced cellulose degradation by targeted integration of a cohesin-fused β-glucosidase into the *Clostridium thermocellum* cellulosome. *PNAS* 109 (26), pp. 10298-10303. DOI: 10.1073/pnas.1202747109.

Kaur, A.; Singh, S.; Singh, R. S.; Schwarz, W. H.; Puri, M. (2010). Hydrolysis of citrus peel naringin by recombinant alpha-L-rhamnosidase from *Clostridium stercorarium*. J. Chem. Technol. Biotechnol. 85:1419-1422

Lehmann, M.; Wyss, M. (2001): Engineering proteins for thermostability: the use of sequence alignments versus rational design and directed evolution. In: *Current opinion in biotechnology* 12 (4), pp. 371-375.

Prawitwong, P.; Waeonukul, R.; Tachaapaikoon, C.; Pason, P.; Ratanakhanokchai, K.; Deng, L. et al. (2013): Direct glucose production from lignocellulose using *Clostridium thermocellum* cultures supplemented with a thermostable β-glucosidase. In: *Biotechnology for biofuels* 6 (1), p. 184. DOI: 10.1186/1754-6834-6-184.

Puri, M. (2000): Production, purification, and characterization of the debittering enzyme naringinase. Biotechnol. Adv. 18: 207-217.

Puri, M.; Kalra, S. (2005): Purification and characterization of naringinase from a newly isolated strain of *Aspergillus niger* 1344 for the transformation of flavonoids. World J. Microbiol. Biotechnol. 21:753-758

Puri M., Kaur A., Schwarz W. H., Singh S., Kennedy J. F. (2011): Molecular characterization and enzymatic hydrolysis of naringin extracted from kinnow peel waste. Int. J. Biol. Macromol. 48:58-62

Schwarz, W. H. (2001): The cellulosome and cellulose degradation by anaerobic bacteria. In: *Applied Microbiology and Biotechnology* 56 (5-6), pp. 634-649. DOI: 10.1007/s002530100710.

Shoham, Y.; Lamed, R.; Bayer, E. A. (1999): The cellulosome concept as an efficient microbial strategy for the degradation of insoluble polysaccharides. In: *Trends in Microbiology* 7 (7), pp. 275-281. DOI: 10.1016/S0966-842X(99)01533-4.

Waeonukul, R.; Kosugi, A.; Tachaapaikoon, C.; Pason, P.; Ratanakhanokchai, K.; Prawitwong, P. et al. (2012): Efficient saccharification of ammonia soaked rice straw by combination of *Clostridium thermocellum* cellulosome and *Thermoanaerobacter brockii* β-glucosidase. In: *Bioresource technology* 107, pp. 352-357. DOI: 10.1016/j.biortech.2011.12.126.

Zverlov, V. V.; Hertel, C.; Bronnenmeier, K.; Hroch, A.; Kellermann, J.; Schwarz, W. H. (2000). The thermostable α-L-rhamnosidase RamA of *Clostridium stercorarium*: biochemical characterization and primary structure of a bacterial α-L-rhamnoside hydrolase, a new type of inverting glycosyl hydrolase. Molec. Microbiol. 35: 173-179.

The invention claimed is:

1. A mutant β-glucosidase polypeptide consisting of the amino acid sequence of SEQ ID NO. 1:

(SEQ ID NO: 1)
MAKFPRDFVWGTATSSYQIEGAVNEDGRTPSIWDTFSKTX$_1$GKTYKGHTG

DVACDHYHRYKEDVEILKEIGVKAYRFSIAWPRIFPEEGKYNPKGMDFYK

KLIDELQKRDIX$_2$PAATIYHWDLPQWAYDKGGGWLNRESIKWYVEYATKL

FEELGDAIPLWITHNEPWCSSILSYGIGEHAPGHKNYREALIAAHHILLS

HGEAVKAFREMNIKGSKIGITLNLTPAYPASEKEEDKLAAQYADGFANRW

FLDPIFKGNYPEDMMELYSKIIGEFDFIKEGDLETISVPIDFLGX$_3$NYYT

RSIVKYDEDSMLKAENVPGPGKRTEMGWEISPESLYDLLKRLDREYTKLP

MYITENGAAFKDEVTEDGRVHDDERIEYIKEHLKAAAKFIGEGGNLKGYF

VWSLMDNFEWAHGYSKRFGIVYVDYX$_4$TQKRILKDSALWYKEVIX$_5$DDGI

ED;

wherein

X$_1$ is selected from E, P, T, M, A, S and G;
X$_2$ is selected from V, K, R and H;
X$_3$ is selected from I, L, M, P, T and A;
X$_4$ is selected from T, E, D, N, Q, M and P; and
X$_5$ is selected from L, R, K and H;
and wherein the mutant β-glucosidase polypeptide does not include the amino acid sequence of the wild type polypeptide of SEQ ID NO: 44;
and wherein said mutant β-glucosidase polypeptide has an increased thermostability, wherein increased thermostability means that the mutant β-glucosidase polypeptide shows a higher specific β-glucosidase enzyme activity at 65° C. or higher for a duration of at least 24 hours compared to the wild type enzyme of SEQ ID NO: 44.

2. The mutant β-glucosidase polypeptide of claim 1 consisting of the amino acid sequence of SEQ ID NO. 2:

(SEQ ID NO: 2)
MAKFPRDFVWGTATSSYQIEGAVNEDGRTPSIWDTFSKTPGKTYKGHTGD

VACDHYHRYKEDVEILKEIGVKAYRFSIAWPRIFPEEGKYNPKGMDFYKK

LIDELQKRDIX$_2$PAATIYHWDLPQWAYDKGGGWLNRESIKWYVEYATKLF

EELGDAIPLWITHNEPWCSSILSYGIGEHAPGHKNYREALIAAHHILLSH

GEAVKAFREMNIKGSKIGITLNLTPAYPASEKEEDKLAAQYADGFANRWF

LDPIFKGNYPEDMMELYSKIIGEFDFIKEGDLETISVPIDFLGX$_3$NYYTR

SIVKYDEDSMLKAENVPGPGKRTEMGWEISPESLYDLLKRLDREYTKLPM

YITENGAAFKDEVTEDGRVHDDERIEYIKEHLKAAAKFIGEGGNLKGYFV

WSLMDNFEWAHGYSKRFGIVYVDYX$_4$TQKRILKDSALWYKEVIX$_5$DDGIED, wherein

X$_2$ is selected from V, K, R and H;
X$_3$ is selected from I, L, M, P, T and A;
X$_4$ is selected from T, E, D, N, Q, M and P; and
X$_5$ is selected from L, R, K and H.

3. The mutant β-glucosidase polypeptide of claim 1 consisting of the amino acid sequence of SEQ ID NO. 3:

(SEQ ID NO: 3)
MAKFPRDFVWGTATSSYQIEGAVNEDGRTPSIWDTFSKTX$_1$GKTYKGHTGD

VACDHYHRYKEDVEILKEIGVKAYRFSIAWPRIFPEEGKYNPKGMDFYKKL

IDELQKRDIKPAATIYHWDLPQWAYDKGGGWLNRESIKWYVEYATKLFEEL

GDAIPLWITHNEPWCSSILSYGIGEHAPGHKNYREALIAAHHILLSHGEAV

KKAFREMNIKGSKIGITLNLTPAYPASEKEEDLAAQYADGFANRWELDPIF

KGNYPEDMMELYSKIIGEFDFIKEGDLETISVPIDFLGX$_3$NYYTRSIVKYD

EDSMLKAENVPGPGKRTEMGWEISPESLYDLLKRLDREYTKLPMYITENGA

AFKDEVTEDGRVHDDERIEYIKEHLKAAAKFIGEGGNLKGYFVWSLMDNFE

WAHGYSKRFGIVYVDYX$_4$TQKRILKDSALWYKEVIX$_5$DDGIED, wherein

X$_1$ is selected from E, P, T, M, A, S and G;
X$_3$ is selected from I, L, M, P, T and A;
X$_4$ is selected from T, E, D, N, Q, M and P; and
X$_5$ is selected from L, R, K and H.

4. The mutant β-glucosidase polypeptide of claim 1 consisting of the amino acid sequence of SEQ ID NO. 5:

(SEQ ID NO: 5)
MAKFPRDFVWGTATSSYQIEGAVNEDGRTPSIWDTFSKTX$_1$GKTYKGHTG

DVACDHYHRYKEDVEILKEIGVKAYRFSIAWPRIFPEEGKYNPKGMDFYK

KLIDELQKRDIX$_2$PAATIYHWDLPQWAYDKGGGWLNRESIKWYVEYATKL

FEELGDAIPLWITHNEPWCSSILSYGIGEHAPGHKNYREALIAAHHILLS

HGEAVKAFREMNIKGSKIGITLNLTPAYPASEKEEDKLAAQYADGFANRW

FLDPIFKGNYPEDMMELYSKIIGEFDFIKEGDLETISVPIDFLGX$_3$NYYT

RSIVKYDEDSMLKAENVPGPGKRTEMGWEISPESLYDLLKRLDREYTKLP

MYITENGAAFKDEVTEDGRVHDDERIEYIKEHLKAAAKFIGEGGNLKGYF

VWSLMDNFEWAHGYSKRFGIVYVDYETQKRILKDSALWYKEVIX$_5$DDGIE

D, wherein

X$_1$ is selected from E, P, T, M, A, S and G;
X$_2$ is selected from V, K, R and H;
X$_3$ is selected from I, L, M, P, T and A; and
X$_5$ is selected from L, R, K and H.

5. The mutant β-glucosidase polypeptide of claim 1 consisting of the amino acid sequence of SEQ ID NO. 6:

(SEQ ID NO: 6)
MAKFPRDFVWGTATSSYQIEGAVNEDGRTPSIWDTFSKTX$_1$GKTYKGHTG

DVACDHYHRYKEDVEILKEIGVKAYRFSIAWPRIFPEEGKYNPKGMDFYK

-continued

```
KLIDELQKRDIX2PAATIYHWDLPQWAYDKGGGWLNRESIKWYVEYATKL

FEELGDAIPLWITHNEPWCSSILSYGIGEHAPGHKNYREALIAAHHILLS

HGEAVKAFREMNIKGSKIGITLNLTPAYPASEKEEDKLAAQYADGFANRW

ELDPIFKGNYPEDMMELYSKIIGEFDFIKEGDLETISVPIDFLGX3NYYT

RSIVKYDEDSMLKAENVPGPGKRTEMGWEISPESLYDLLKRLDREYTKLP

MYITENGAAFKDEVTEDGRVHDDERIEYIKEHLKAAAKFIGEGGNLKGYF

VWSLMDNFEWAHGYSKRFGIVYVDYX4TQKRILKDSALWYKEVIRDDGIE

D,
``` wherein
$X_1$ is selected from E, P, T, M, A, S and G;
$X_2$ is selected from V, K, R and H;
$X_3$ is selected from I, L, M, P, T and A; and
$X_4$ is selected from T, E, D, N, Q, M and P.

6. The mutant β-glucosidase polypeptide of claim 1 consisting of:
the amino acid sequence of SEQ ID NO: 9.

7. The mutant β-glucosidase polypeptide of claim 1 selected from the group consisting of:
the amino acid sequence of SEQ ID NO: 13;
the amino acid sequence of SEQ ID NO: 16;
the amino acid sequence of SEQ ID NO: 19; and
the amino acid sequence of SEQ ID NO: 20.

8. The mutant β-glucosidase polypeptide of claim 1 selected from the group consisting of:
the amino acid sequence of SEQ ID NO: 22;
the amino acid sequence of SEQ ID NO: 26;
the amino acid sequence of SEQ ID NO: 28;
the amino acid sequence of SEQ ID NO: 29; and
the amino acid sequence of SEQ ID NO: 31.

9. The mutant β-glucosidase polypeptide of claim 1 selected from the group consisting of:
the amino acid sequence of SEQ ID NO: 32;
the amino acid sequence of SEQ ID NO: 33;
the amino acid sequence of SEQ ID NO: 35; and
the amino acid sequence of SEQ ID NO: 36.

10. The mutant β-glucosidase polypeptide of claim 1, consisting of the amino acid sequence of SEQ ID NO: 37.

11. A nucleic acid, which encodes a mutant β-glucosidase polypeptide of SEQ ID NOs: 9, and 37.

12. A recombinant polynucleotide molecule comprising the nucleic acid according to claim 11 plus expression-controlling elements operably linked with said nucleic acid to drive expression thereof.

13. An expression vector comprising the nucleic acid according to claim 11.

14. An isolated host cell comprising a nucleic acid which codes for a mutant β-glucosidase polypeptide according to claim 1.

15. The isolated host cell of claim 14 comprising a nucleic acid which encodes a mutant β-glucosidase polypeptide of SEQ ID NOs: 9, 20, 31, 36 and 37.

16. A process for producing a mutant β-glucosidase polypeptide, which process comprises culturing the host cell of claim 14 under culture conditions suitable for the expression of said mutant polypeptide.

17. The process of claim 16, wherein said mutant β-glucosidase polypeptide is expressed in said host cell and said process further includes the step of recovering the polypeptide or a fragment thereof from the culture.

18. Artificial cellulosome comprising the mutant β-glucosidase polypeptide according to claim 1.

19. Method for the degradation of cellulosic biomass comprising the steps of:
a) mixing at least one mutant β-glucosidase polypeptide of SEQ ID NOs: 9, 20, 31, 36 and 37 or an artificial cellulosome comprising at least one mutant β-glucosidase polypeptide of SEQ ID NOs: 9, 20, 31, 36 and 37 with cellulosic biomass or insoluble cellulose; and enzymatically hydrolyzing cellulosic biomass or insoluble cellulose under thermophilic conditions.

20. Composition comprising the mutant β-glucosidase polypeptide according to claim 1.

21. Composition comprising the artificial cellulosome of claim 18.

22. The host cell of claim 14 comprising an expression vector which comprises a nucleic acid which encodes a mutant β-glucosidase polypeptide of SEQ ID NOs: 9, 20, 31, 36 and 37.

* * * * *